(12) United States Patent
Roblyer et al.

(10) Patent No.: US 10,768,165 B2
(45) Date of Patent: Sep. 8, 2020

(54) SYSTEMS AND METHODS FOR MEASURING WATER AND LIPID CONTENT IN TISSUE SAMPLES

(71) Applicant: TRUSTEES OF BOSTON UNIVERSITY, Boston, MA (US)

(72) Inventors: Darren Roblyer, Jamaica Plain, MA (US); Yanyu Zhao, Pasadena, CA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 16/376,561

(22) Filed: Apr. 5, 2019

(65) Prior Publication Data

US 2019/0310239 A1  Oct. 10, 2019

Related U.S. Application Data

(60) Provisional application No. 62/653,362, filed on Apr. 5, 2018.

(51) Int. Cl.
*G01N 33/483* (2006.01)
*G01N 21/27* (2006.01)
(Continued)

(52) U.S. Cl.
CPC ........ *G01N 33/4833* (2013.01); *G01N 21/27* (2013.01); *G01N 21/359* (2013.01); *G01N 21/3554* (2013.01); *G01N 21/4738* (2013.01); *G01N 21/49* (2013.01); *G01N 2021/1757* (2013.01); *G01N 2021/1765* (2013.01); *G01N 2201/0675* (2013.01); *G01N 2201/12* (2013.01)

(58) Field of Classification Search
None
See application file for complete search history.

(56) References Cited

U.S. PATENT DOCUMENTS

| | | |
|---|---|---|
| 2003/0184757 A1 | 10/2003 | Bevilacqua |
| 2006/0129037 A1* | 6/2006 | Kaufman ............. A61B 5/1455 600/322 |

(Continued)

OTHER PUBLICATIONS

International Search Report and Written Opinion of International Searching Authority in International Patent Application No. PCT/US2019/026067, dated Jul. 10, 2019 (10 pages).

(Continued)

*Primary Examiner* — Edwin C Gunberg
(74) *Attorney, Agent, or Firm* — Nixon Peabody LLP

(57) ABSTRACT

An imaging system for measuring water and blood lipid content in a tissue sample includes a light source configured to emit a plurality of sequential wavelengths of light within a predetermined range of wavelengths, a spatial modulation device configured to direct each of the plurality of sequential wavelengths of light onto a tissue sample plane to generate a first plurality of patterns on the issue sample plane at a first spatial frequency and a second plurality of patterns on the tissue sample plane at a second spatial frequency, an imaging device configured to generate first image data reproducible as images the first plurality of patterns and second image data reproducible as images the second plurality of patterns, and a controller configured to determine a first optical property and a second optical property for each location on the sample plane.

26 Claims, 13 Drawing Sheets

(51) Int. Cl.
G01N 21/3554 (2014.01)
G01N 21/359 (2014.01)
G01N 21/49 (2006.01)
G01N 21/47 (2006.01)
G01N 21/17 (2006.01)

(56) References Cited

U.S. PATENT DOCUMENTS

| | | |
|---|---|---|
| 2006/0184043 A1 | 8/2006 | Tromberg |
| 2008/0101657 A1* | 5/2008 | Durkin ............. G01J 3/02 382/110 |
| 2009/0118622 A1 | 5/2009 | Durkin |
| 2009/0318815 A1 | 12/2009 | Barnes |
| 2014/0213910 A1* | 7/2014 | Durkin ............. A61B 5/0075 600/477 |
| 2015/0374276 A1 | 12/2015 | Farkas |
| 2016/0278678 A1 | 9/2016 | Valdes |
| 2016/0302669 A1 | 10/2016 | Cuccia |
| 2017/0209089 A1 | 7/2017 | Warren |

OTHER PUBLICATIONS

Mazhar et al., "Wavelength optimization for rapid chromophore mapping using spatial frequency domain imaging"; J Biomed Opt. 15(6): 061716, Dec. 23, 2010. [Online]. Available: http://citeseerx.ist.psu.edu/viewdoc/download?doi=10.1.1.865.353&rep=rep1&type=pdf (9 pages).
Applegate, M. et al.; "High-speed spatial frequency Domain Imaging (SFDI) with temporally modulated light"; Journal of Biomedical Optics, 22(7), 076019 (2017) (8 pages).
Tabassum, S. et al.; "Feasibility of spatial frequency domain imaging (SFDI) for optically characterizing a preclinical oncology model"; Biomedical Optics Express 7(10), 4154-4170 (2016) (17 pages).
Zhao, Y. et al.; "angle correction for small animal tumor imaging with spatial frequency domain imaging (SFDI)"; Biomedical Optics Express 7(6), 2373-2384 (2016) (12 pages).
Zhao, Y. et al.; "Spatial mapping of fluorophore quantum yield in diffusive media"; Journal of Biomedical Optics 20(8), 086013; Aug. 2015 (8 Pages).
Cuccia, D. J. et al., "Quantitation and mapping of tissue optical properties using modulated imaging," J. Biomed. Optics 14(2), 024012 (2009). (31 Pages).
Ponticorvo, A.A., et al.; "Quantitative assessment of partial vascular occlusions in a swine pedicle flap model using spatial frequency domain imaging," Biomed. Opt. Express 4(2), 298-306 (2013). (9 Pages).
Yafi, A. et al.; "Postoperative quantitative assessment of reconstructive tissue status in a cutaneous flap model using spatial frequency domain imaging," Plast. Reconstr. Surg. 127(1), 117-130 (2011).(19 Pages).
Nadeau, K. P. et al.; "Quantitative assessment of renal arterial occlusion in a porcine model using spatial frequency domain imaging," Opt. Lett. 38(18), 3566-3569 (2013). (8 Pages).
Gioux, S. et al.; "First-in-human pilot study of a spatial frequency domain oxygenation imaging system," J. Biomed. Opt. 16(8), 086015 (2011).(11 Pages).
Lin, A. J. et al.; "Spatial frequency domain imaging of intrinsic optical property contrast in a mouse model of Alzheimer's disease," Ann. Biomed. Eng. 39(4),1349-1357 (2011).(9 Pages).
Cuccia, D.J. et al.; "Modulated imaging: quantitative analysis and tomography of turbid media in the spatial-frequency domain," Opt. Lett. 30(11), 1354-1356 (2005).(3 Pages).
Nadeau, K. P. et al.; "Multifrequency synthesis and extraction using square wave projection patterns for quantitative tissue imaging," J. Biomed. Opt. 20(11), 116005 015).(11 Pages).
Roblyer, D. et al.; "Optical imaging of breast cancer oxyhemoglobin flare correlates with neoadjuvant chemotherapy response one day after starting treatment"; Proc. Natl. Acad. Sci. U.S.A., 108, pp. 14626-14631 (2011).(15 Pages).

Papadopoulos, M. C. et al.; "Molecular mechanisms of brain tumor edema"; Neuroscience 129, 1011-1020 (2004).(10 Pages).
Peetla, C. et al.; "Biophysics of cell membrane lipids in cancer drug resistance: Implications for drug transport and drug delivery with nanoparticles"; J. Biol. Chem. 102, 38-53 (2013) (29 Pages).
Egeblad, M. et al.; "Dynamic interplay between the collagen scaffold and tumor evolution"; Curr. Opin. Cell Biol. 22, 697-706 (2010).(17 Pages).
Walker-Samuel, S. et al.; "In vivo imaging of glucose uptake and metabolism in tumors"; Nat Med 19, 1067-1072 (2013). (18 Pages).
Kienle, A. et al.; "Spatially resolved absolute diffuse reflectance measurements for noninvasive determination of the optical scattering and absorption coefficients of biological tissue"; Opt. (1996). (11 Pages).
Bevilacqua, F. et al.; "Broadband absorption spectroscopy in turbid media by combined frequencydomain and steady-state methods"; Appl. Opt. 39,6498 (2000). (10 Pages).
Cerussi, A. et al.; "In vivo absorption, scattering, and physiologic properties of 58 malignant breast tumors determined by broadband diffuse optical spectroscopy"; J. Biomed. Opt. 11, 44005 (2015). (16 Pages).
Mazhar, A. et al.; "Noncontact imaging of burn depth and extent in a porcine model using spatial frequency domain imaging"; J. Biomed. Opt. 19, 20901 (2014). (11 Pages).
Wilson, R. H. et al.; "Review of short-wave infrared spectroscopy and imaging methods for biological tissue characterization"; J. Biomed. Opt. 20, 30901 (2015).(11 Pages).
Wilson, R. H. et al.; "Quantitative short-wave infrared multispectral imaging of in vivo tissue optical properties"; J. Biomed. Opt. 19, 86011 (2014).(5 Pages).
Nguyen, J. Q. et al.; "Spatial frequency domain imaging of burn wounds in a preclinical model of graded burn severity"; J. Biomed. Opt. 18, 66010 (2013).(8 Pages).
Weber, J. R. et al.; "Multispectral imaging of tissue absorption and scattering using spatial frequency domain imaging and a computed-tomography imaging spectrometer"; J. Biomed Opt 16, 11015 (2011).(7 Pages).
Beckman Laser Institute; "NIR Tissue Absorption"; available at: http://dosi.bli.uci.edu/research/. (3 Pages).
Allen, T. J. et al.; "Spectroscopic photoacoustic imaging of lipid-rich plaques in the human aorta in the 740 to 1400 nm wavelength range"; J. Biomed. Opt. 17, 61209 (2012).(11 Pages).
Meacham, C. E. et al.; "Tumour heterogeneity and cancer cell plasticity"; Nature 501, 328-337 (2013).(25 Pages).
Marusyk, A. et al.; "Intra-tumour heterogeneity: a looking glass for cancer?"; Nat. Rev. Cancer 12, 323-334 (2012).(12 Pages).
Siu, L. et al.; "Toward understanding and exploiting tumor heterogeneity"; 21, 846-853 (2016).(19 Pages).
Bedard, P. L. et al.; "Tumour heterogeneity in the clinic"; Nature 10, 4173-4183 (2013).(25 Pages).
Burrell, R. A. et al.; "The causes and consequences of genetic heterogeneity in cancer evolution"; Nature 501, 338-345(2013).(8 Pages).
Chechi, K. et al.; "Brown adipose tissue as an anti-obesity tissue in humans"; Obes. Rev. 15, 92-106 (2014).(15 Pages).
Bartelt, A. et al.; "Adipose tissue browning and metabolic health"; Nat. Rev. Endocrinol. 10, 24-36 (2014).(13 Pages).
Mann, A. et al.; Localization, Identification, and Excision of Murine Adipose Depots; J. Vis. Exp. 1-7 (2014). doi:10.3791/52174 (7 Pages).
Cypess, A. M. et al.; "Identification and Importance of Brown Adipose Tissue in Adult Humans"; N. Engl. J. Med. 360, 1509-1517 (2009).(12 Pages).
Bordone, L. et al.; "Calorie restriction, SIRT1 and metabolism: understanding longevity"; Nat. Rev. Mol. Cell Biol. 6, 298-305 (2005).(8 Pages).
Giralt, M. et al.; White, brown, beige/brite: Different adipose cells for different functions?; Endocrinology 154, 2992-3000 (2013).(9 Pages).
Ishibashi, J. et al.; "Beige Can Be Slimming"; Science (80-. ). 328, 1113-1114 (2010).(4 Pages).
Deng, Y. et al.; Differences Help Recognition: A Probabilistic Interpretation; PLoS One 8, (2013).(10 Pages).

(56) References Cited

OTHER PUBLICATIONS

Bishop, C. M.; "Pattern Recognition and Machine Learning"; Journal of Chemical Information and Modeling 53, (2013).(758 Pages).

Merritt, S. et al.; "Comparison of water and lipid content measurements using diffuse optical spectroscopy and MRI in emulsion phantoms"; *Technol. Cancer Res. Treat.* 2,563-9 (2003). (7 Pages).

Fischer, A. H. et al.; "Hematoxylin and eosin staining of tissue and cell sections"; *Cold Spring Haab. Protoc.* 655-658 (2008). doi:10.1101/pdb.prot073411(3 Pages).

Ramirez-Zacarias, J. L. et al.; "Quantitation of adipose conversion and triglycerides by staining intracytoplasmic lipids with oil red O"; *Histochemistry* 493-497 (1992). (6 Pages).

Weissleder, R.; "A clearer vision for in vivo imaging"; *Nat. Biotechnol.* 19,316-317 (2001). (2 Pages).

Cerussi, A. E. et al.; "Diffuse optical spectroscopic imaging correlates with final pathological response in breast cancer neoadjuvant chemotherapy"; *Philos. Trans. A. Math. Phys. Eng. Sci.* 369,4512-30 (2011).(19 Pages).

Bi, P. et al.; Inhibition of Notch signaling promotes browning of white adipose tissue and ameliorates obesity; *Nat. Med.* 20,911-918 (2014).(22 Pages).

Nguyen, J. T. et al.; "A Novel Pilot Study Using Spatial Frequency Domain Imaging to Assess Oxygenation of Perforator Flaps During Reconstructive Breast Surgery"; *Ann. Plast. Surg.* 71,308-315 (2013). (17 Pages).

Rohrbach, D. J. et al.; "Preoperative mapping of nonmelanoma skin cancer using spatial frequency domain and ultrasound imaging"; *Acad. Radiol.* 21,263-70 (2014).(17 Pages).

\* cited by examiner

SYSTEMS AND METHODS FOR MEASURING WATER AND LIPID CONTENT IN TISSUE SAMPLES

CROSS-REFERENCE TO RELATED APPLICATIONS

This application claims the benefit of and priority to U.S. Provisional Application No. 62/653,362, filed on Apr. 5, 2018, which is hereby incorporated by reference herein in its entirety.

STATEMENT REGARDING FEDERALLY SPONSORED RESEARCH

This invention was made with Government Support under Contract No. W81XWH-15-1-0070 awarded by the Department of the Army. The Government has certain rights in this invention.

TECHNICAL FIELD

The present disclosure relates generally to imaging systems and methods, and more particularly, to systems and methods for determining water and/or lipid content in a tissue sample.

BACKGROUND

Between about 60% to 80% of the human body comprises water and lipids, which are important for proper cellular function. Alterations in the water and/or lipid content in tissue is associated with many adverse health conditions, such as, for example, cardiovascular disease, inflammation, diabetes, and many cancers. For example, lipid heterogeneity in a tumor is a relevant biomarker for cancer diagnosis. Clinical assessment of water and lipid levels in tissue often utilizes magnetic resonance imaging ("MRI"), which can generate tomographic images of water and lipids with T1 and T2 weighted scans. However, the use of MRIs to assess water and lipid levels in most clinical applications is often limited by the high costs of MRIs. Moreover, MRI images can only provide a semi-quantitative assessment of water and lipid levels. It would be advantageous to provide systems and methods capable of providing quantitative measurements of water and lipids in in-in vivo tissue to support the study and clinical assessment of a wide variety of health conditions. The present disclosure is directed to solving these and other problems.

SUMMARY

According to some implementations of the present disclosure, a method for measuring water and lipid content in a tissue sample includes generating, using a light source and a spatial modulation device, a first plurality of patterns at a first spatial frequency on a tissue sample plane and a second plurality of patterns at a second spatial frequency on the tissue sample plane for a first wavelength of light from a plurality of sequential wavelengths of light, the light source being configured to emit the plurality of sequential wavelengths of light within a predetermined range of wavelengths, obtaining, using an imaging device, (i) first image data reproducible as images of the first plurality of patterns at the first spatial frequency for the first wavelength of light and (ii) second image data reproducible as images of the second plurality of patterns at the second spatial frequency for the first wavelength of light, generating, using a controller, a first demodulated image for the first wavelength of light based on the first image data, determining, using the controller, a first diffuse reflectance value for each of a plurality of locations on the tissue sample plane at the first wavelength of light based on the first demodulated image, generating, using the controller, a second demodulated image for the first wavelength of light based on the second image data, determining, using the controller, a second diffuse reflectance value for each of the plurality of locations on the tissue sample plane for the first wavelength of light based on the second demodulated image, and determining, using the controller, based on the first diffuse reflectance value and the second diffuse reflectance value, (i) a first optical property and (ii) a second optical property for each of the plurality of locations on the tissue sample plane for the first wavelength of light.

According to some implementations of the present disclosure, an imaging system for measuring water and blood lipid content in a tissue sample includes a light source configured to emit a plurality of sequential wavelengths of light at a predetermined interval, each of the plurality of sequential wavelengths of light being within a predetermined range of wavelengths, a spatial modulation device configured to direct each of the plurality of sequential wavelengths of light emitted from the light source onto a tissue sample plane and cause each of the plurality of sequential wavelengths of light to generate, (i) a first plurality of patterns on the issue sample plane at a first spatial frequency, the first plurality of patterns including a first pattern having a first phase, a second pattern having a second phase, and a third pattern having a third phase, and (ii) a second plurality of patterns on the tissue sample plane at a second spatial frequency, the second plurality of patterns including a first pattern having the first phase, a second pattern having the second phase, and a third pattern having the third phase, an imaging device configured to generate (i) first image data reproducible as images of each of the first plurality of patterns and (ii) second image data reproducible as images each of the second plurality of patterns, and a controller including one or more processors and one or more memory devices, at least one of the one or more memory devices storing computer-readable instructions configured to cause at least one of the one or more processors to: generate, using the first image data, a first demodulated image associated with the first spatial frequency for each of the plurality of sequential wavelengths of light, determine a first diffuse reflectance value for each of a plurality of locations on the tissue sample plane for each of the plurality of sequential wavelength based on the first demodulated image, generate, using the second image data, a second demodulated image associated with the second spatial frequency for each of the plurality of sequential wavelengths of light, determine a second diffuse reflectance value for each of the plurality of locations on the tissue sample plane for each of the plurality of sequential wavelength based on the second demodulated image, and determine, based on the first diffuse reflectance value and the second diffuse reflectance value, (i) a first optical property and (ii) a second optical property for each of the plurality of locations on the sample plane for each of the plurality of sequential wavelengths of light.

The above summary is not intended to represent each embodiment or every aspect of the present invention. Additional features and benefits of the present invention are apparent from the detailed description and figures set forth below.

Figure 1:
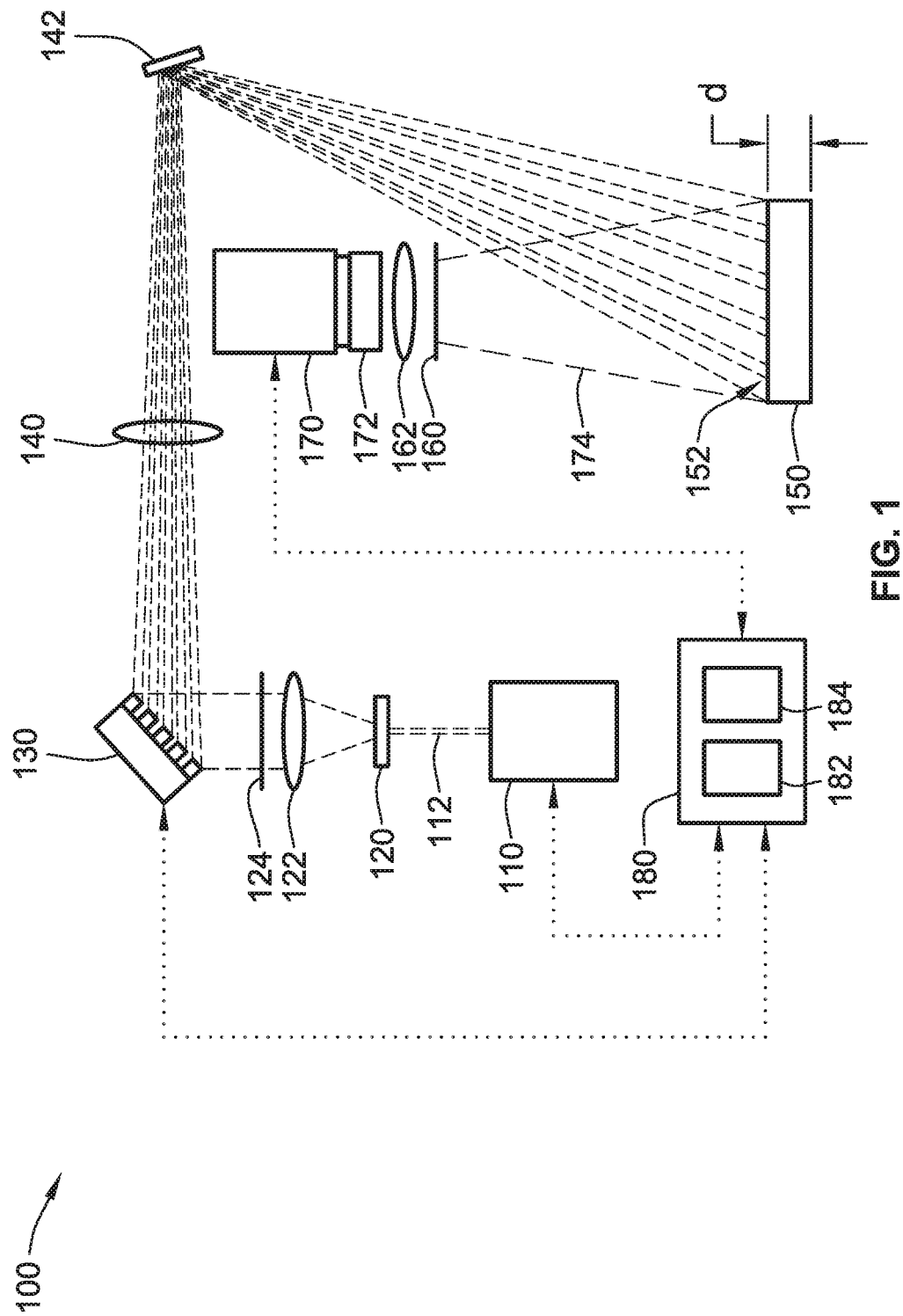
FIG. 1 is a schematic illustration of an imaging system according to some implementations of the present disclosure.

While the disclosure is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Many non-invasive, so-called "label-free" systems and methods utilize wavelengths of light to image in-vivo tissue (e.g., image tissue without using a contrast agent). For example, visible spectroscopy ("VIS") techniques use light having wavelengths between 400 nm and 700 nm to image tissue. In another example, near infrared spectroscopy ("NIRS") techniques use light having wavelengths between 700 nm and 900 nm to quantify oxy-hemoglobin and deoxy-hemoglobin content in, for example, oncologic and brain imaging applications. NIRS techniques exploit the relatively weak optical attenuation of light within an NIR optical window, which enables imaging depths of only several millimeters for widefield imaging. These VIS and NIR techniques are limited in quantifying water and lipid levels in in-vivo tissue due to the dominating effect of hemoglobin absorption within the wavelengths used by VIS and NIR. In contrast to hemoglobin, water and lipids each have distinct optical absorption characteristics at shortwave infrared wavelengths ("SWIR") that are between about 900 nm and about 2,000 nm.

As described above, alterations in the water and/or lipid content in tissue are associated with many adverse health conditions. The role of water and lipids as stand-alone biomarkers of these conditions has been underappreciated. In fact, the prior imaging techniques described above often seek to prevent light absorption by water in the tissue by avoiding the SWIR wavelengths. Further, conventional imaging devices (e.g., silicon-based cameras) used in connection with prior imaging techniques typically lack the spectral sensitivity necessary to detect wavelengths greater than 1,000 nm. That is, conventional imaging devices (e.g., silicon-based cameras) cannot detect most or all of the SWIR spectrum. Another obstacle to imaging water and lipids is that both optical absorption and scattering of light in the tissue sample contribute to the resulting image contrast, obscuring distinctions between various chromophores (e.g., hemoglobin, water, lipids, etc.) in the tissue sample.

Referring to FIG. 1, an imaging system 100 for measuring water and/or lipid content in a tissue sample is illustrated. The imaging system 100 includes a light source 110, a spatial modulation device 130, an imaging device 170, and a controller 180. As described in further detail herein, the imaging system 100 is generally used to image a sample 150 and quantify water and lipid content in the tissue sample 150 (e.g., by generating one or more graphs). The tissue sample 150 can be, for example, an in-vivo tissue sample from a mammal (e.g., a human) or an ex-vivo tissue sample from a mammal (e.g., a human).

The light source 110 emits a plurality of sequential wavelengths of light, each of which is within a predetermined range of wavelengths. More specifically, the predetermined range of wavelengths includes at least a portion of the SWIR spectrum described above. For example, the predetermined range of wavelengths can be between about 700 nm and about 2,500 nm, between about 900 nm and about 2,000 nm, between about 900 nm and about 2,500 nm, etc. Preferably, the predetermined range of wavelengths is between about 900 nm and about 2,000 nm.

The light source 110 also emits the plurality of sequential wavelengths of light within the predetermined range of wavelengths at a predetermined interval. That is, the difference in the wavelength of each successive one of sequential plurality of wavelengths of light is defined by the predetermined interval. The predetermined interval can be, for example, an interval between about 0.1 nm and about 50 nm, between about 1 nm and about 20 nm, between about 2 nm and 10 nm, about 5 nm, etc. For example, if the predetermined range of wavelengths is between about 900 nm and 1,300 nm and the predetermined interval is 5 nm, the light source 110 emits a first wavelength of light at 900 nm, a second wavelength of light at 905 nm, a third wavelength of light at 910 nm, and so on, through the upper end of the predetermined range of wavelengths of light (e.g., 1,300 nm).

In some implementations, the light source 110 is a laser that emits a plurality of beams, such as beam 112 shown in FIG. 1. In such implementations, the light source 110 can tune the wavelength of the beam 112 such that the wavelength of the beam 112 is within the predetermined range discussed above (e.g., between about 900 nm and about 2,000 nm). More generally, the light source 110 can emit a beam 112 at a wavelength outside of the predetermined range (e.g., the light source 110 is configured to emit a beam 112 having a wavelength between about 680 nm and about 1,300 nm). Further, the light source 110 emits a plurality of beams 112 at the predetermined interval discussed above. The light source 110 can emit the beam 112 as a pulse having a predetermined duration (e.g., between about 25 femtoseconds [fs] and about 250 fs, between about 50 fs and about 150, about 120 fs, etc.) at a predetermined repetition rate (e.g., between about 20 MHz and about 100 MHz, between about 40 MHz and about 80 MHz, etc.) As one example, in some implementations, the light source 110 is an InSight DS+ laser manufactured by Spectra-Physics of Santa Clara, Calif. (USA).

While the light source 110 has been described and shown herein as being a laser, more generally, the light source 110 can be any wavelength tunable light source that is configured to emit light. For example, the light source 110 can be a broadband lamp. In such implementations, the imaging system 100 also includes one or more bandpass optical filters (not shown) configured tune the light emitted from the broadband lamp to be within the predetermined range of wavelengths of light described herein. (e.g., within the SWIR spectrum). Similarly, while the light source 110 has been described herein as being tunable (e.g., such that one can control the what wavelengths of light are emitted from the light source 110), alternatively, the imaging system 100 can include one or more filters (not shown) that are positioned between the light source 110 and the imaging device 170. In such implementations, the one or more filters control the wavelength of light that is reflected onto the sample 150 (e.g., such that the wavelength is within the predetermined range of wavelengths described herein). As another example, the light source 110 can include one or more light-emitting diodes (LED's), each of which is configured to a wavelength of light or range of wavelengths of light. For example, a first LED or group of LEDs can be configured to emit a first wavelength of light or a first range of wavelengths of light and a second LED or group of LEDs can be configured to emit a second wavelength of light or a second range of wavelengths of light, such that the one or more LEDs collectively are configured to emit the entire predetermined range of wavelengths of light described herein (e.g., sequentially).

As shown in FIG. 1, each beam 112 emitted from the light source 110 is directed towards the spatial modulation device 130. The spatial modulation device 130 then directs the beam 112 towards the tissue sample 150, as described in further detail herein. In some implementations, the imaging system 100 can further include a diffuser 120, a collimating lens 122 and a first polarizer 124, each of which is generally positioned between the light source 110 and the spatial modulation device 130. As shown in FIG. 1, the diffuser 120 increases the diameter of the beam 112 emitted from the light source 110 as it passes through the diffuser 120 before the beam 112 reaches the spatial modulation device 130. The diffuser 120 can be configured to increase the diameter of the beam 112 by, for example, between about 1.1 times and about 100 times, between about 2 times and about 50 times, between about 10 times and about 30 times, etc. The collimating lens 122 is positioned between the diffuser 120 and the spatial modulation device 130. The collimating lens 122 is used to collimate the beam 112 and generally aids in focusing the beam 112 onto the spatial modulation device 130. The first polarizing lens 124 is positioned between the collimating lens 122 and the spatial modulation device 130 and is generally used to reduce specular reflection. The first polarizing lens 124 can be a crossed linear polarizer, such as, for example, a VersaLight™ polarizer, manufactured by Meadowlark Optics of Frederick, Colo. (USA).

The spatial modulation device 130 is configured to control one more properties of each beam 112 emitted from the light source 150 as it is directed towards the tissue sample 150. More specifically, the spatial modulation device 130 is used to control the phase of each of the beams 112 as they are reflected towards the tissue sample 150 and the spatial frequency of each of the beams 112 as they are reflected towards the tissue sample 150. As described in further detail herein, changing the spatial frequency and/or the phase of the beam 112 causes a different reflectance pattern to be formed on the tissue sample 150.

The spatial modulation device 130 can shift the phase of the plurality of sequential wavelengths of light by a predetermined value (e.g., 120 degrees) one or more times. For example, for a first wavelength of light at 900 nm, the spatial modulation device 130 can cause a first phase shift of 120 degrees such that the phase of first wavelength of light is now 120 degrees and a second phase shift of 120 degrees such that the phase of the first wavelength of light is now 240 degrees. In other words, the spatial modulation device 130 causes each of plurality of sequential wavelengths of light to be reflected on the tissue sample 150 at a first phase (e.g., 0 degrees), a second phase (e.g., 120 degrees), and a third phase (e.g., 240 degrees). As described in further detail herein, each of phase shift causes a corresponding shift in the resulting pattern formed on the tissue sample 150 for each of the plurality of sequential wavelengths of light.

The spatial modulation device 130 also shifts the spatial frequency of each of the plurality of sequential wavelengths of light. For example, for each of the plurality of sequential wavelengths of light, the spatial modulation device 130 causes the light to reach the sample plane 150 at a first spatial frequency and a second spatial frequency that is greater than the first spatial frequency. The first spatial frequency can be, for example, 0 mm$^{-1}$. The second spatial frequency can be, for example, between about 0.01 mm$^{-1}$ and about 0.5 mm$^{-1}$, between about 0.05 mm$^{-1}$ and about 0.2 mm$^{-1}$, between about 0.075 mm$^{-1}$ and about 0.125 mm$^{-1}$, etc. Preferably, the second spatial frequency is about 0.1 mm$^{-1}$, which aids in separating the effects of absorption and scattering, as described in further detail herein.

In some implementations, the spatial modulation device 130 is a microelectromechanical ("MEMS") device including one or more digital micromirrors. Each digital micromirror is configured to reflect light and manipulate one or more properties of the reflected light (e.g., the phase and/or spatial frequency). The digital micromirror(s) are actuated (e.g., using a voltage input, a thermal input, an electrothermal input, a magnetic input, etc.) to manipulate, for example, the phase of the reflected light. The spatial modulation device 130 can include, for example, 1 or more micromirrors, 10 or more micromirrors, 100 or more micromirrors, 1,000 or more micromirrors, 10,000 or more micromirrors, 100,000 or more micromirrors, etc. As one example, in some implementations, the spatial modulation device 130 is a CEL550 Light Engine manufactured by Digital Light Innovations of Austin, Tex. (USA).

In some implementations, the imaging system 100 can further include a first lens 140 and one or more mirrors 142 that are positioned between the spatial modulation device 130 and the tissue sample 150. For example, as shown in FIG. 1, the first lens 140 is positioned between the spatial modulation device 130 and the one or more mirrors 142, and the one or more mirrors 142 are positioned between the first lens 140 and the tissue sample 150. The first lens 140 has a focal length and magnifies the light reflected from the spatial modulation device 130. The focal length of the first lens 140 can be, for example, between about 10 mm and about 200 mm, about 25 mm and about 100 mm, about 75 mm, etc.

The one or more mirrors 142 cause the light (e.g., beam 112) reflected from the spatial modulation device 130 and passing through the first lens 140 to be directed onto a sample plane 152 of the tissue sample 150. The tissue sample plane 152 is the upper surface of the tissue sample 150, which as shown in FIG. 1, has a sample depth d. As shown in FIG. 1, the reflected light from the spatial modulation device 130 that passes through the first lens 140 is generally perpendicular to the tissue sample plane 152. The one or more mirrors 142 are positioned relative to the spatial modulation device 130 and the tissue sample 150 such that the one or more mirrors 142 cause the light reflected from the spatial modulation device 130 to be directed onto the tissue sample plane 152 of the tissue sample 150.

While the one or more mirrors 142 is shown in FIG. 1 as including one mirror, in some implementations, the one or more mirrors 142 can include a plurality of mirrors (e.g., two mirrors, three mirrors, four mirrors, ten mirrors, etc.) to aid in directing the light reflected from the spatial modulation device 130 onto the tissue sample plane 152. Further, while the one or more mirrors 142 are shown in FIG. 1 as being positioned between the spatial modulation device 130 and the tissue sample 150, alternatively, at least one of the one or more mirrors 142 can be positioned between the light source 110 and the spatial modulation device 130 to aid in directing the light (e.g., beam 112) emitted from the light source 110 towards the spatial modulation device 130. For example, a first group of one or more mirrors can be positioned between the light source 110 and the spatial modulation device 130 to aid in directing light from the light source 110 onto the spatial modulation device 130, and a second group of one or more mirrors can be positioned between the spatial modulation device 130 and the tissue sample 150.

The imaging device 170 generates image data reproducible as images of the reflectance pattern on the tissue sample plane 152 formed by the plurality of sequential wavelengths of light described herein. As shown, the imaging device 170 is positioned such that the tissue sample plane 152 is within a field of view 174 of the imaging device 170. The field of view 174 of the imaging device 170 can be, for example, between about 8 cm by about 6 cm and about 30 cm by about 30 cm. Each image generated by the imaging device 170 comprises a plurality of pixels, which, as described in further detail herein, can be analyzed by the controller 180 to determine, for example, diffuse reflectance values.

As described above, the plurality of sequential wavelengths of light emitted by the light source 110 that are reflected onto the tissue sample plane 152 are within a predetermined range of wavelengths of light, which includes at least a portion of the SWIR spectrum. Thus, the spectral sensitivity of the imaging device 170 is such that the imaging device 170 can detect wavelengths of light within the predetermined range of wavelengths of light. Unlike conventional silicon-based cameras which can typically only detect wavelengths up to about 1,000 nm, the imaging device 170 detect wavelengths within the SWIR spectrum (e.g., wavelengths between about 300 nm and about 1,600 nm, wavelengths between about 900 nm and about 1,300 nm, etc.).

In some implementations, the imaging device 170 is a germanium-doped CMOS camera having a spectral sensitivity between about 300 nm and about 1,600 nm. In such implementations, the imaging device 170 can generate images that are 640 pixels by 480 pixels with a pixel pitch of 10 μm. In one example, the imaging device 170 is a TriWave germanium-doped CMOS camera manufactured by Infrared Laboratories, Inc. of Peabody, Mass. (USA). In another example, the imaging device 170 can be an Indium Gallium Arsenide (InGaAs) imaging device. Other imaging devices that can accomplish the desired imaging results are also contemplated.

As shown in FIG. 1, in some implementations, the imaging system 100 can further include a second polarizer 160 and a second lens 160, each of which is positioned between the tissue sample plane 152 and the imaging device 170. As shown in FIG. 1, the second polarizer 160 is positioned between the tissue sample plane 152 and the second lens 162, and the second lens 162 is positioned between the second polarizer 162 and the imaging device 170. The second polarizer 160 is the same as, or similar to, the first polarizer 124 described herein. The second lens 162 is the same as, or similar to, the first lens 140 described herein.

The controller 180 includes one or more processors 182 (hereinafter, "processor 182") and one or more memory devices 184 (hereinafter, "memory device 184"). As shown, the controller 180 is communicatively coupled (e.g., via a wired connection or a wireless connection) to the light source 110, the spatial modulation device 130, and the imaging device 170 to control the operation of these components. As described in further detail herein, the controller 180 also receives and processes image data from by the imaging device 170 to determine, for example, the water and/or lipid content in the tissue sample 150. The processor 182 can be a general or special purpose processor or microprocessor, and the controller 180 can include any suitable number of processors (e.g., one processor, a plurality of processors, etc.) The memory device 184 can be any suitable computer readable storage device or media, such as, for example, a random or serial access memory device, a hard drive, a solid state drive, a flash memory device, etc. In some implementations, the controller 180 also includes a display device (e.g., a display monitor, a touchscreen, LED display, LCD display, etc.)

While the imaging system 100 has been illustrated to include each of the components shown in FIG. 1, alternative imaging systems that are the same as, or similar to, the imaging system 100 can be constructed with more or less components. For example, a first alternative imaging system (not shown) includes the light source 110, the spatial modulation device 130, the imaging device 170, and the controller 180. As another example, a second alternative imaging system (not shown) includes the light source 110, the diffuser 120, the collimating lens 122, the spatial modulation device 130, the first lens 140, the imaging device 170, the controller 180, and two mirrors 142.

Figure 2:
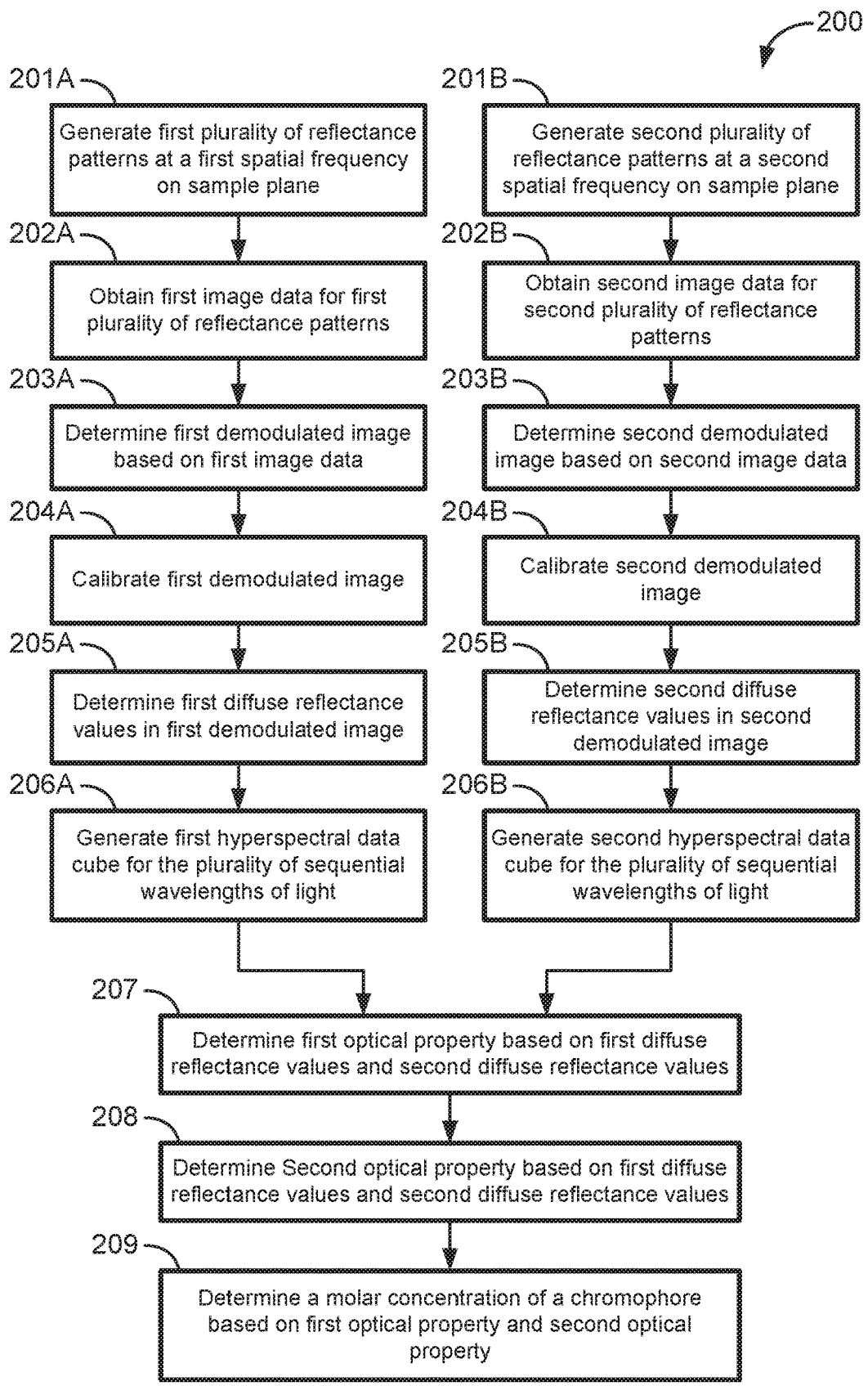
FIG. 2 is a process flow diagram illustrating a method for measuring water and lipid content in a tissue sample according to some implementations of the present disclosure.

Referring to FIG. 2, a method 200 for measuring water and/or lipid content in a tissue sample (e.g., tissue sample 150) is illustrated. The method 200 can be implemented using the imaging system 100 or any of the alternative imaging systems described herein. The tissue sample can be, for example, an in-vivo tissue sample from a mammal (e.g., a human) or an ex-vivo tissue sample from a mammal (e.g., a human).

Figure 3A:
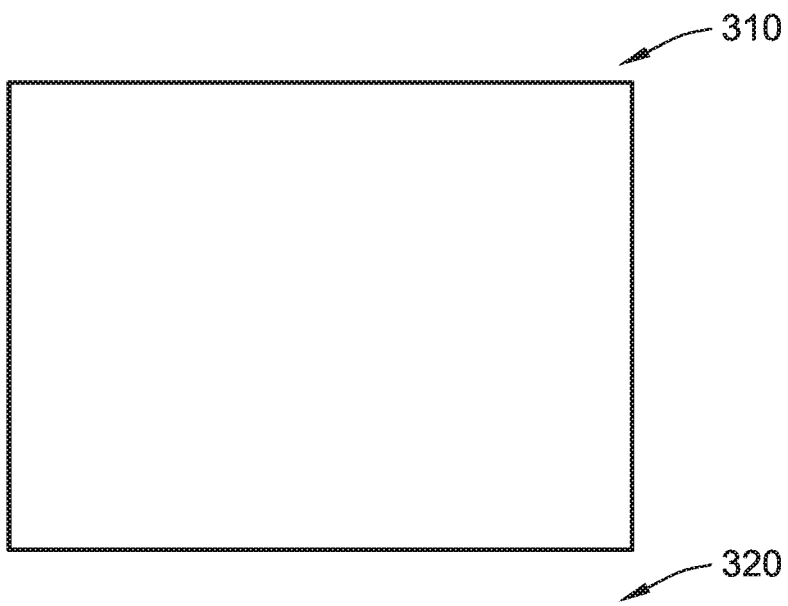
FIG. 3A illustrates a first reflectance pattern having a first phase and a first spatial frequency according to some implementations of the present disclosure.
Figure 3B:
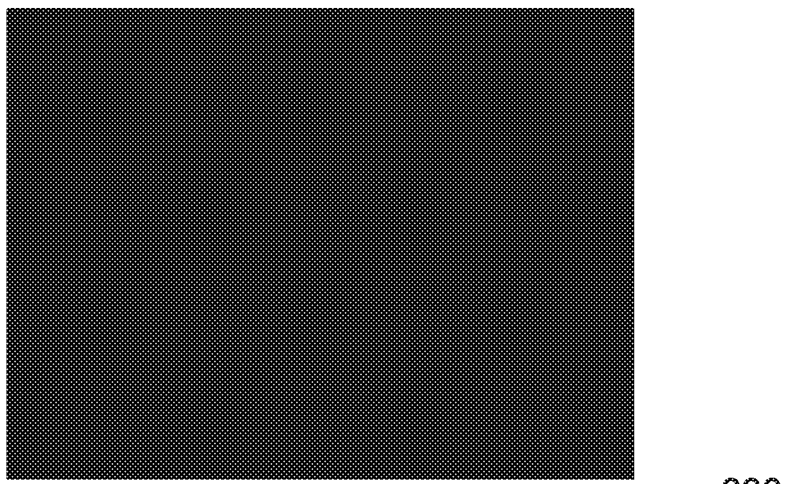
FIG. 3B illustrates a second reflectance pattern having a second phase and the first spatial frequency according to some implementations of the present disclosure.
Figure 3C:
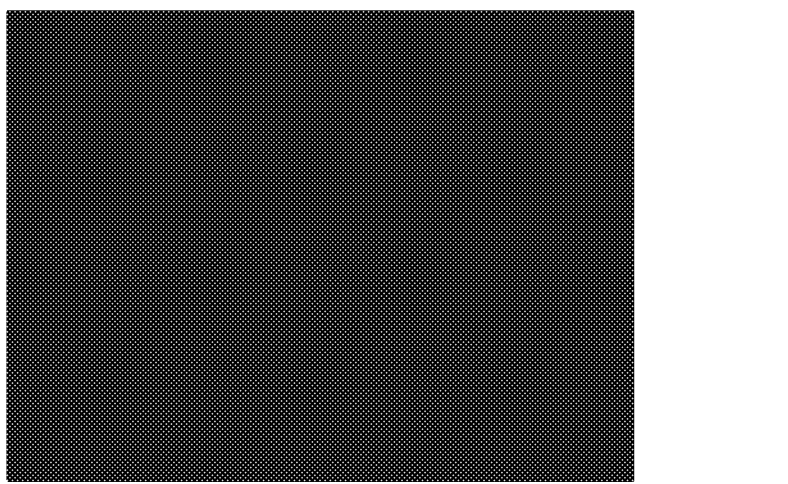
FIG. 3C illustrates a third reflectance pattern having a third phase and the first spatial frequency according to some implementations of the present disclosure.

Step 201A of the method 200 includes generating, using the light source 110 and the spatial modulation device 130 (FIG. 1), a first plurality of reflectance patterns on the tissue sample plane 152 at a first spatial frequency. As described herein, the spatial modulation device 130 can control the spatial frequency of the beam 112 and shift the phase of the beam 112 before the beam reaches the tissue sample plane 152. Referring to FIGS. 3A-3C, the first plurality of reflectance patterns includes three patterns: a first reflectance pattern 310 having a first phase (FIG. 3A), a second reflectance pattern 320 having a second phase (FIG. 3B), and a third reflectance pattern 330 having a third phase (FIG. 3B). In the illustrated example, the first phase is 0 degrees, the second phase is 120 degrees, and the third phase is 240 degrees. The spatial modulation device 130 causes the phase shift in second reflectance pattern 320 (FIG. 3B) relative to the first reflectance pattern 310 (FIG. 3A), and the phase shift in the third reflectance pattern 330 (FIG. 3C) relative to the second reflectance pattern 320 (FIG. 3B). The first spatial frequency in the illustrated examples of FIG. 3A-3C is 0 mm$^{-1}$. When the spatial frequency is zero, the period of the wave is zero, meaning that each reflectance pattern in the first plurality of reflectance patterns has a planar pattern.

Figure 4A:
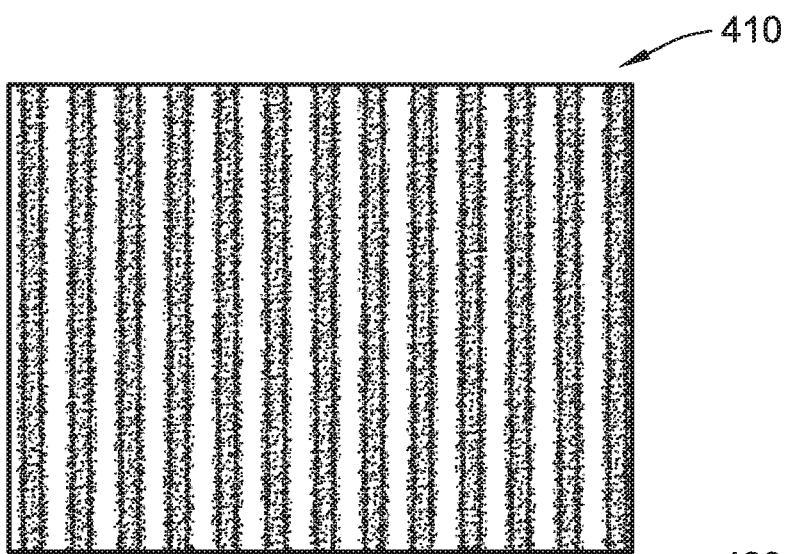
FIG. 4A illustrates a first reflectance pattern having a first phase and a second spatial frequency according to some implementations of the present disclosure.
Figure 4B:
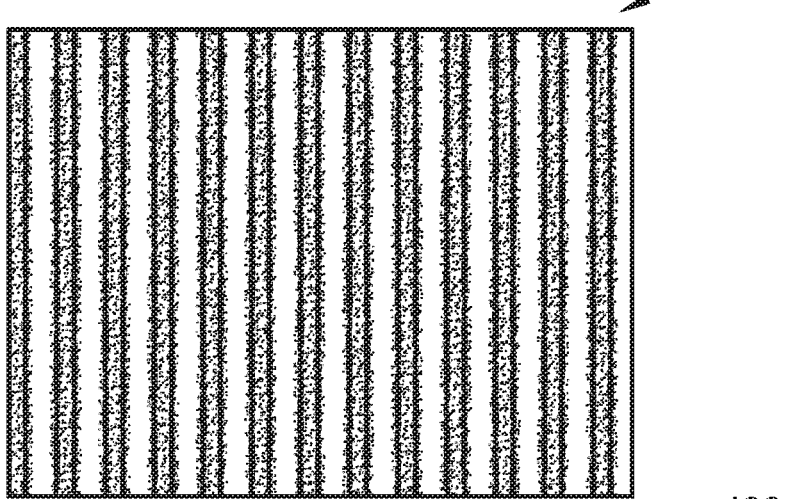
FIG. 4B illustrates a second reflectance pattern having the second phase and the second spatial frequency according to some implementations of the present disclosure.
Figure 4C:
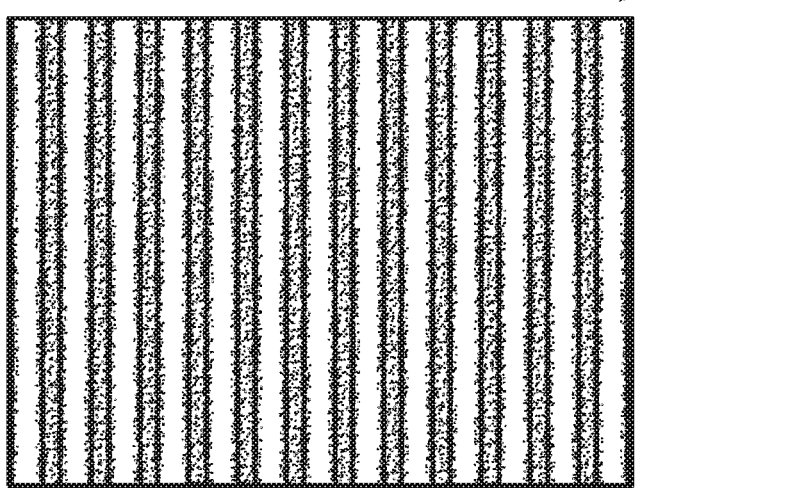
FIG. 4C illustrates a third reflectance pattern having the third phase and the second spatial frequency according to some implementations of the present disclosure.

Step 201B of the method 200 is similar to step 201A, and includes generating, using the light source 110 and the spatial modulation device 130 (FIG. 1), a second plurality of reflectance patterns on the tissue sample plane 152 at a second spatial frequency. Referring to FIGS. 4A-4C, the second plurality of reflectance patterns includes three patterns: a first reflectance pattern 410 having a first phase (FIG. 4A), a second reflectance pattern 420 having a second phase (FIG. 4B), and a third reflectance pattern 430 having a third phase (FIG. 4B). The first phase, the second phase, and the third phase of the second plurality of reflectance patterns are the same as the first phase, the second phase, and the third phase of the first plurality of reflectance patterns—0 degrees, 120 degrees, and 240 degrees, respectively. The second plurality of reflectance patterns (FIGS. 4A-4C) differ from the first plurality of reflectance patterns (FIGS. 3A-3C) in that the second spatial frequency is greater than the first spatial frequency. In the illustrated examples of FIGS. 4A-4C, the second spatial frequency is 0.1 mm$^{-1}$, although other spatial frequency values are possible, as described herein. Unlike a spatial frequency of zero (i.e., where the period of the wave is zero), the non-zero second spatial frequency causes each of the second plurality of reflectance patterns to have a sinusoidal pattern (FIGS. 4A-4C), as opposed to a planar pattern (FIGS. 3A-3C). Additionally, as described in further detail below, the second spatial frequency is sensitive to an optical scattering property, whereas the first spatial frequency is sensitive to both an optical scattering property and an optical absorption property.

While step 201A is generally described herein as including generating a plurality of reflectance patterns (e.g., three) at the first spatial frequency on the sample plane, in some implementations, step 201A includes generating a single reflectance pattern. Likewise, step 201B can also include generating a single reflectance pattern on the sample plane. And while the reflectance patterns for the second spatial frequency are shown as being sinusoidal in FIGS. 4A-4C, more generally, the reflectance patterns for the second spatial frequency can have other patterns, such as, for example, square, circular, etc.

Step 202A of the method 200 includes obtaining, using the imaging device 170 (FIG. 1), first image data reproducible as images of each of the first plurality of reflectance patterns generated on the tissue sample plane 152 during step 201A. More specifically, the first image data is reproducible as a first image of at least a portion of the first reflectance pattern 310 (FIG. 3A), a second image of at least a portion of the second reflectance pattern 320 (FIG. 3B), and a third image of at least a portion of the third reflectance pattern 330 (FIG. 3C). The first image data is received and stored in the memory device 184 of the controller 180 for processing during step 203A.

Step 202B of the method 200 is similar to step 202A and includes obtaining, using the imaging device 170 (FIG. 1), second image data reproducible as images of each of the second plurality of reflectance patterns generated on the tissue sample plane 152 during step 201B. More specifically, the second image data is reproducible as a first image of at least a portion of the first reflectance pattern 410 (FIG. 4A), a second image of at least a portion of the second reflectance pattern 420 (FIG. 4B), and a third image of at least a portion of the third reflectance pattern 430 (FIG. 4C). The second image data is received and stored in the memory device 184 of the controller 180 for processing during step 203B.

Figure 5A:
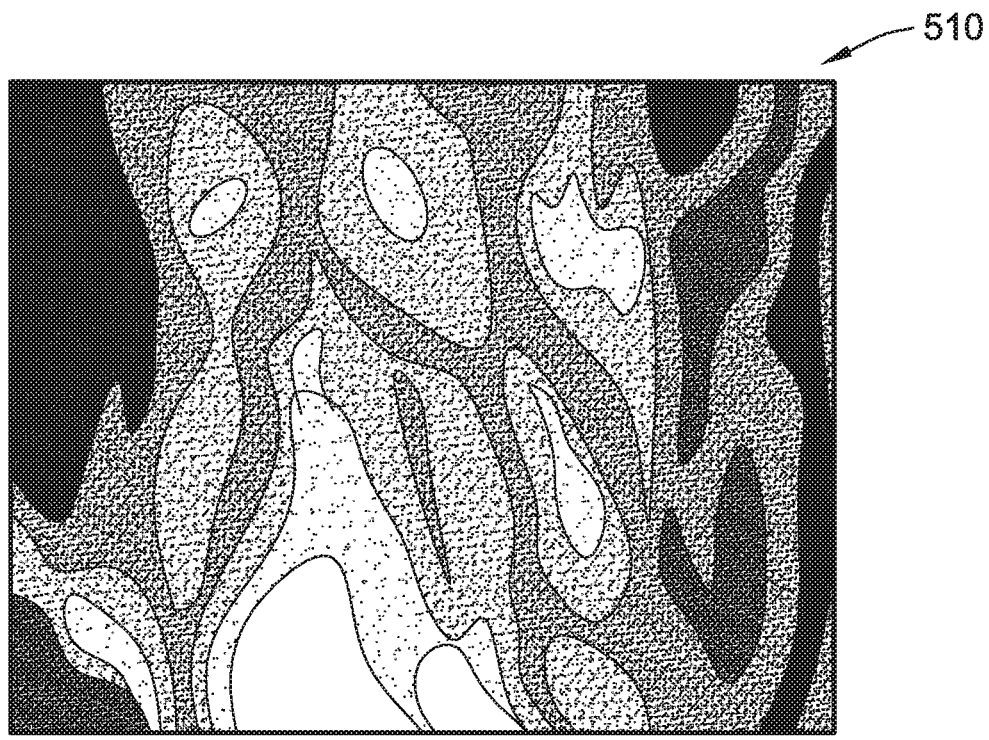
FIG. 5A illustrates a first demodulated image associated with the first spatial frequency according to some implementations of the present disclosure.

Step 203A of the method 200 includes determining, using the processor 182 of the controller 180 (FIG. 1), a first demodulated image associated with the first spatial frequency based on the first image data obtained during step 202A. An exemplary first demodulated image 510 that was determined based on the reflectance patterns in FIGS. 3A-3C is illustrated in FIG. 5A. More specifically, the first image of the first reflectance pattern 310 (FIG. 3A), the second image of the second reflectance pattern 320 (FIG. 3B), and the third image of the third reflectance pattern (FIG. 3C) are combined to generate the first demodulated image 510 (FIG. 5A).

In some implementations, the first demodulated image 510 (FIG. 5A) is determined in step 203A using equation 1, provided below:

$$I = \frac{\sqrt{2}}{3}\sqrt{((I_1 - I_2)^2 + (I_2 - I_3)^2 + (I_3 - I_1)^2)} \qquad \text{Equation 1}$$

In equation 1, "I" is the intensity of the first demodulated image, "$I_1$" is the intensity of the first image of the first reflectance pattern 310 at the first phase (FIG. 3A), "$I_2$" is the intensity of the second image of the second reflectance pattern 320 at the second phase (FIG. 3B), and "$I_3$" is the intensity of the third image of the third reflectance pattern 330 at the third phase (FIG. 3C).

In other implementations, step 203A includes using a neural network algorithm to determine the first demodulated image 510 (FIG. 5A) based on the first image data, rather than equation 1. In such implementations, the neural network is trained (e.g., using a machine learning algorithm) with a training data set that includes raw images (e.g., images that are the same as or similar to FIGS. 3A-3C and FIGS. 4A-4C) and demodulated images (e.g., images that are the same as or similar to FIGS. 5A and 5B). The training data set can be generated using light propagation models, such as Monte-Carlo simulations. After being trained using the training data, the neural network is able to accept raw images and generate demodulate images in the same or similar manner as described above using equation 1. In still other implementations, step 203A includes using a Hilbert Transform methodology to determine the first demodulated image 510 (FIG. 5A).

Figure 5B:
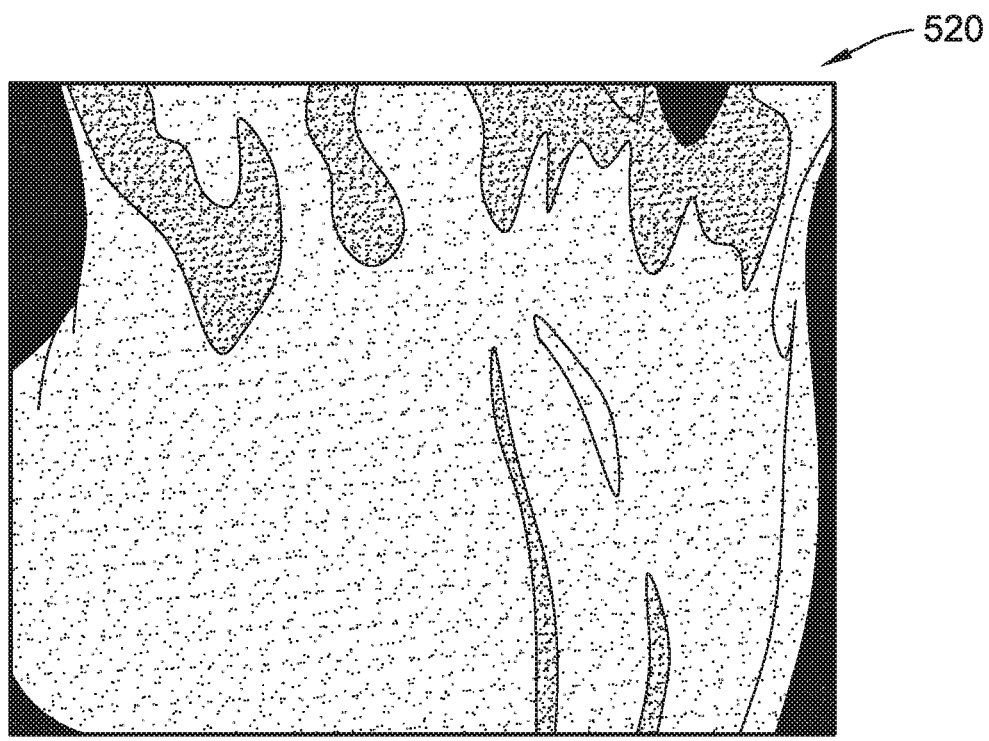
FIG. 5B illustrates a second demodulated image associated with the second spatial frequency according to some implementations of the present disclosure.

Step 203B of the method 200 is similar to step 203A described above and includes determining, using the processor 182 of the controller 180 (FIG. 1), a second demodulated image associated with the second spatial frequency based on the second image data obtained during step 202B. An exemplary second demodulated image 520 that was determined based on the reflectance patterns in FIGS. 4A-4C is illustrated in FIG. 5B. More specifically, the first image of the first reflectance pattern 410 (FIG. 4A), the second image of the second reflectance pattern 420 (FIG. 4B), and the third image of the third reflectance pattern 430 (FIG. 4C) are combined to generate the second demodulated image 520 (FIG. 5B). The second demodulated image 520 can be determined, for example, using equation 1 described above, where, "I" is the intensity of the second demodulated image, "$I_1$" is the intensity of the first image of the first reflectance pattern 410 at the first phase (FIG. 4A), "$I_2$" is the intensity of the second image of the second reflectance pattern 420 at the second phase (FIG. 4B), and "$I_3$" is the intensity of the third image of the third reflectance pattern 430 at the third phase (FIG. 4C).

Figure 6:
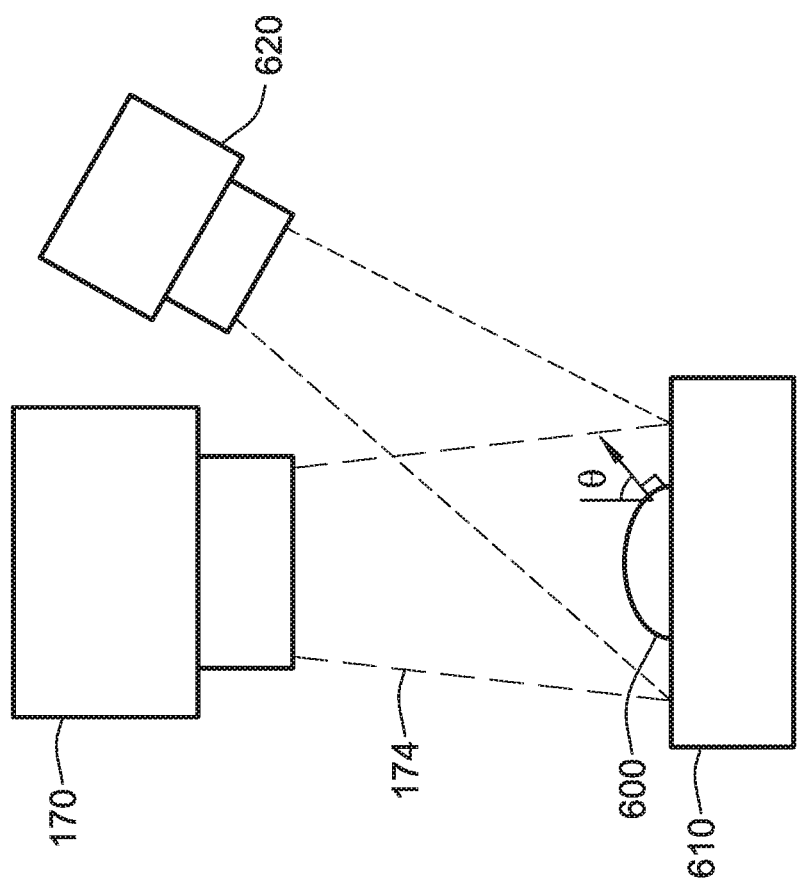
FIG. 6 is a schematic illustration of a phantom for determining an instrument response function of the imaging system of FIG. 1 according to some implementations of the present disclosure.

Step 204A of the method 200 includes calibrating the first demodulated image (e.g., the first demodulated image 510 of FIG. 5A) to remove potential artifacts (e.g., an anomaly in the image of the sample tissue that is not actually in the sample tissue itself) caused by the instrumentation in the imaging system 100. To calibrate the first demodulated image, an instrument response function (often referred to as "IRF") is removed from the first demodulated image. The IRF is the mapping between the incoming photon flux and the detected events and depends on not only the hardware of the imaging system, but also the processing that calculates whether a measured event is a photon. Referring to FIG. 6, the instrument response function is determined using the imaging device 170, a phantom 600, a background phantom 610, and a light projector 620. The instrument response function can be determined prior to any of the steps of the method 200 are performed. The phantom 600 has one or more predetermined optical properties, including a predetermined scattering property and a predetermined absorption property. As shown, the phantom 600 has a hemispheric shape and can comprise silicon and an absorbing dye, for example. The light projector 620 projects light having one or more predetermined properties (e.g., a predetermined wavelength, a predetermined spatial frequency, a predetermined phase, or any combination thereof) onto the phantom 600, and the imaging device 170 obtains phantom image data reproducible as images of at least a portion of the phantom 600. Based on the phantom image data and the predetermined optical properties of the phantom 600, the processor 182 of the controller 180 (FIG. 1) determines the instrument response function. This determined instrument response function is then subtracted from the first demodulated image during step 204A to obtain a first demodulated and calibrated image.

Step 204B of the method 200 is similar to step 204A and includes calibrating the second demodulated image (e.g., the second demodulated image 520 of FIG. 5B). The second demodulated image is calibrated by subtracting the instrument response function described above from the second demodulated image in the same or similar manner as the instrument response function is subtracted from the first demodulated image during step 204A.

Step 205A of the method 200 includes determining, using the controller 180 (FIG. 1), first diffuse reflectance values (Rd) in the first demodulated and calibrated image obtained during step 204A. As described above, each image obtained using the imaging device 170 comprises a plurality of pixels (e.g., tens of thousands of pixels). Likewise, the first demodulated and calibrated image comprises a plurality of pixels. During step 205A, the controller 180 (FIG. 1) of the imaging system 100 determines a first diffuse reflectance value for each of the pixels in the first demodulated and calibrated image. In some implementations, the first diffuse reflectance value for each of the pixels is scaled between 0 and 1. That is, each of the pixels in the first demodulated and calibrated image is associated a value between 0 and 1 that is indicative of a first diffuse reflectance value of that pixel. In other implementations, a first diffuse reflectance value can be determined for groups or sections of pixels (e.g., two, five, ten, twenty, etc.) within the first demodulated and calibrated image, rather than each individual pixel.

Step 205B of the method 200 includes determining, using the controller 180 (FIG. 1), second diffuse reflectance values (Rd) in the second demodulated and calibrated image obtained during step 204B. Similar to step 205A, step 205B includes determining a second diffuse reflectance value for each of the pixels in the second demodulated and calibrated image. Like the first demodulated and calibrated image, each of the pixels in the second demodulated and calibrated image is associated with a value between 0 and 1 that is indicative of a second diffuse reflectance value of that pixel.

Steps 201A-205A are repeated for each of the plurality of sequential wavelengths of light emitted from the light source 110. For example, steps 201A-205A are performed a first time for a first wavelength of light (e.g., 900 nm), a second time for a second wavelength of light (e.g., 905 nm), and so on until steps 201A-205A are repeated for each of the plurality of sequential wavelengths of light (e.g., up to a wavelength of 1,300 nm). Likewise, steps 201B-205B are repeated for each of the plurality of sequential wavelengths of light described herein. After steps 201A-205A and 201B-205B are repeated, the memory device 184 of the imaging system 100 will have stored therein (i) a first demodulated and calibrated image associated with the first spatial frequency for each of the plurality of sequential wavelengths of light and (ii) a second demodulated and calibrated image associated with the second spatial frequency for each of the plurality of sequential wavelengths of light. For example, for a first wavelength of light (e.g., 900 nm), the memory device 184 of the controller 180 (FIG. 1) stores a first demodulated and calibrated image associated with the first spatial frequency and a second demodulated and calibrated image associated with the second spatial frequency, and for a second wavelength of light (e.g., 1,300 nm), the memory device 184 of the controller 180 (FIG. 1) stores a first demodulated and calibrated image associated with the first spatial frequency and a second demodulated and calibrated image associated with the second spatial frequency. The exemplary wavelengths provided above and elsewhere are to for illustrative purposes only and are not meant to be limiting.

Figure 7A:
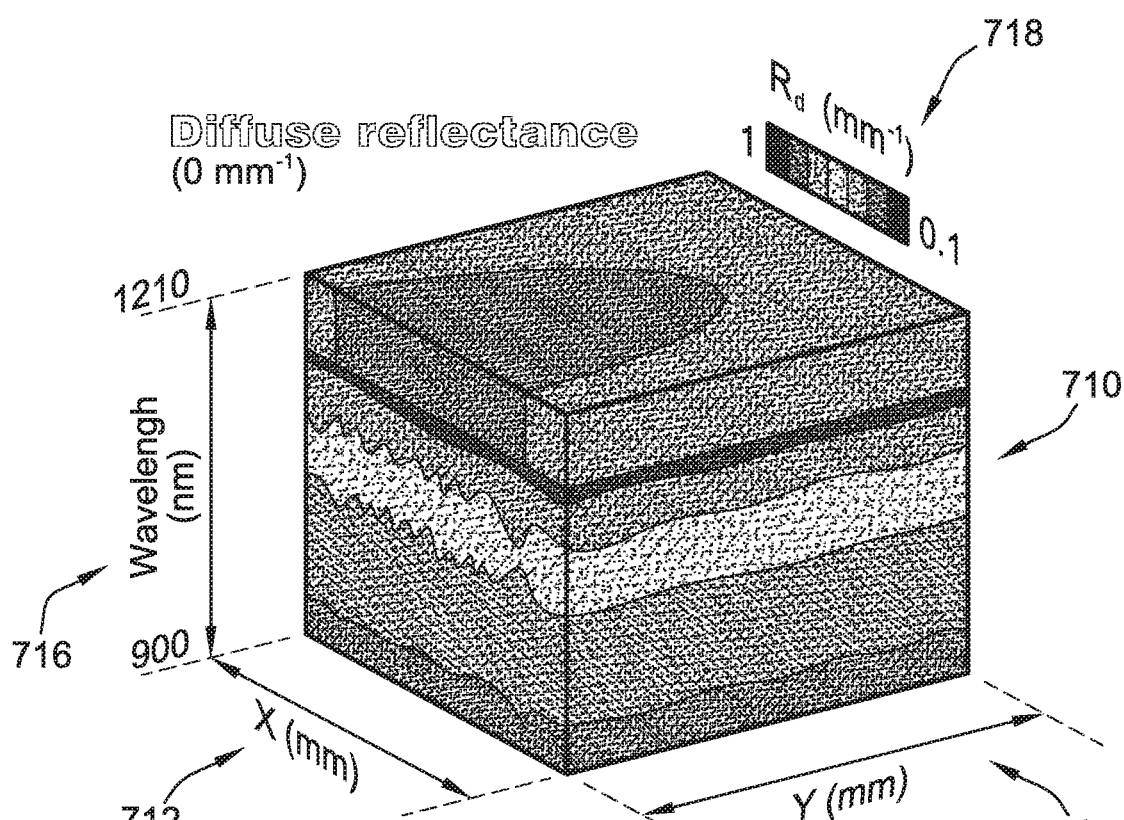
FIG. 7A illustrates a first hyperspectral data cube indicative of diffuse reflectance values for the first spatial frequency according to some implementations of the present disclosure.

Step 206A of the method 200 includes generating a first hyperspectral data cube associated with the first spatial frequency for the plurality of sequential wavelengths of light. An exemplary hyperspectral data cube 710 associated with the first spatial frequency is illustrated in FIG. 7A. As shown, the first hyperspectral data cube 710 includes a first axis 712 indicative of an x-coordinate on the tissue sample plane 152 (FIG. 1), a second axis 714 indicative of a y-coordinate on the tissue sample plane 152, and a third axis 716 indicative of the plurality of sequential wavelengths of light. Each of the plurality of sequential wavelengths is associated with a different sample depth d (FIG. 1), or z-coordinate within the tissue sample 150. Thus, the first hyperspectral data cube 710 is a three-dimensional representation of the tissue sample 150. The first hyperspectral data cube 710 also includes a plurality of colors that are indicative of the first diffuse reflectance value at each location within the tissue sample 150. For example, a legend 718 is used to indicate the color (e.g., violet) that is indicative of the lowest first diffuse reflectance value (e.g., 0.1) and the color (e.g., red) that is indicative of the highest first diffuse reflectance values (e.g., 1), with colors between violet and red being indicative of first diffuse reflectance values between the highest and lowest values (e.g., between 0.1 and 1). Alternatively, as shown, the first hyperspectral data cube 710 can use textures or other indicia that are indicative of the first diffuse reflectance values.

Figure 7B:
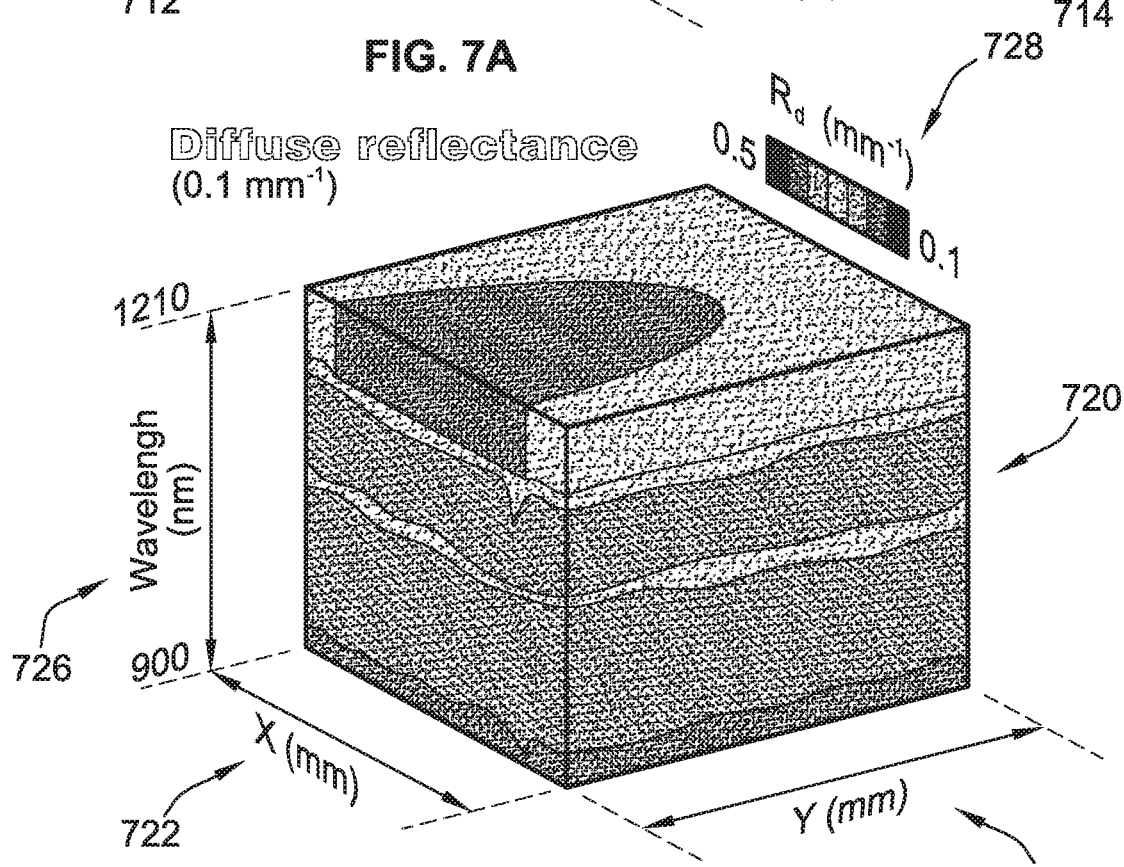
FIG. 7B illustrates a second hyperspectral data cube indicative of diffuse reflectance values for the second spatial frequency according to some implementations of the present disclosure.

Step 206B of the method 200 is similar to step 206A and includes generating a second hyperspectral data cube associated with the second spatial frequency for the plurality of sequential wavelengths of light. An exemplary hyperspectral data cube 720 associated with the second spatial frequency is illustrated in FIG. 7B. The second hyperspectral data cube 720 includes a first axis 722 indicative of an x-coordinate on the tissue sample plane 152 (FIG. 1), a second axis 724 indicative of a y-coordinate on the tissue sample plane 152, and a third axis 726 indicative of the plurality of sequential wavelengths of light. Each of the plurality of sequential wavelengths is associated with a different sample depth d (FIG. 1), or z-coordinate within the tissue sample 150. Thus, the second hyperspectral data cube 720 is a three-dimensional representation of the tissue sample 150. The second hyperspectral data cube 720 also includes a plurality of colors that are indicative of the second diffuse reflectance value at each location within the tissue sample 150. An exemplary legend 728 is used to indicate the color (e.g., violet) that is indicative of the lowest second diffuse reflectance value (e.g., 0.1) and the color (e.g., red) that is indicative of the highest second diffuse reflectance values (e.g., 0.5), with colors between violet and red being indicative of second diffuse reflectance values between the highest and lowest values (e.g., between 0.1 and 0.5). Alternatively, as shown, the second hyperspectral data cube 720 can use textures or other indicia that are indicative of the second diffuse reflectance values.

Step 207 of the method 200 includes determining a first optical property at each location in the tissue sample 150 based on the first diffuse reflectance values associated with the first spatial frequency and the second diffuse reflectance values associated with the second spatial frequency. The first optical property can be, for example, an absorption property (a). In some implementations, step 207 includes generating a third hyperspectral data cube indicative of the first optical property based on the first hyperspectral data cube 710 indicative of the first diffuse reflectance values for the first spatial frequency (FIG. 7A) and the second hyperspectral data cube 720 indicative of the second diffuse reflectance values for the second spatial frequency (FIG. 7B).

Figure 8A:
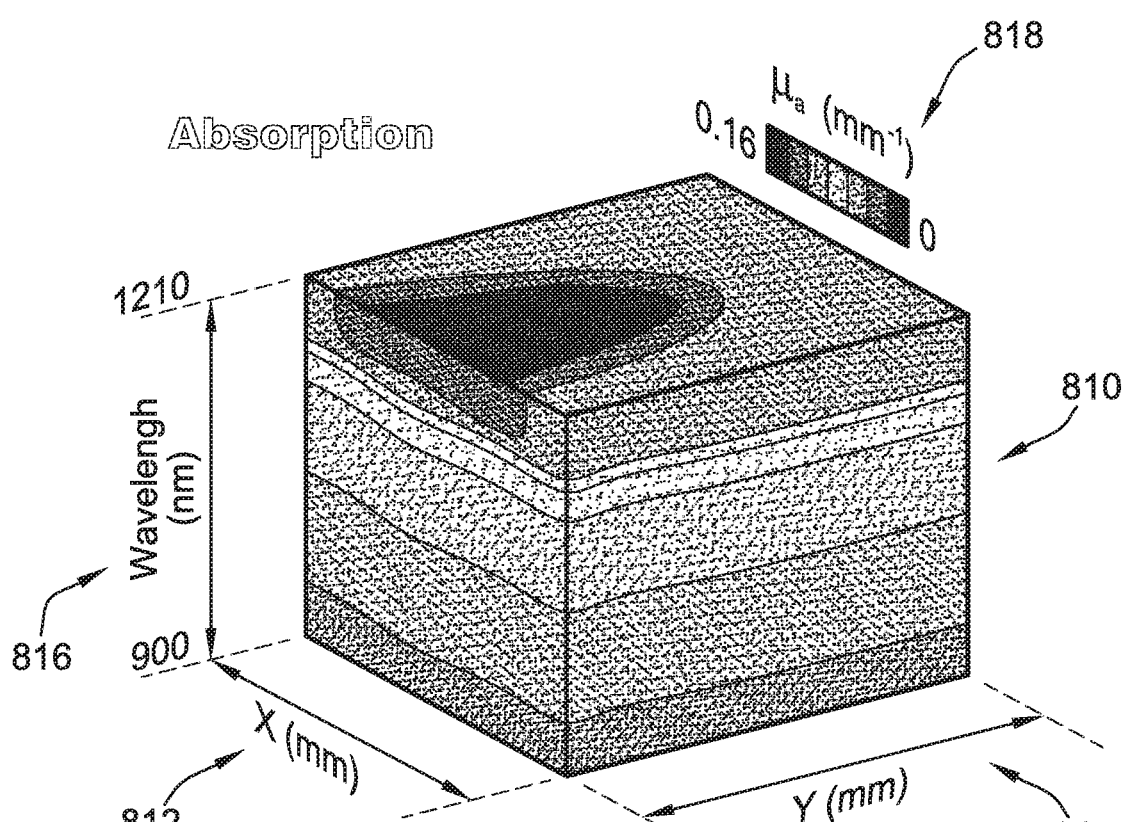
FIG. 8A illustrates a third hyperspectral data cube indicative of absorption property values according to some implementations of the present disclosure.

Referring to FIG. 8A, an exemplary third hyperspectral data cube 810 indicative of the first optical property, in this example an absorption property $\mu_a$, is illustrated. The third hyperspectral data cube 810 includes a first axis 812 indicative of an x-coordinate on the tissue sample plane 152 (FIG. 1), a second axis 814 indicative of a y-coordinate on the tissue sample plane 152, and a third axis 816 indicative of the plurality of sequential wavelengths of light. The third hyperspectral data cube 810 also includes a plurality of colors that are indicative of first optical property at each location within the tissue sample 150, which in this example is an absorption property value. An exemplary legend 818 indicates the color (e.g., violet) that is indicative of the lowest first optical property value (e.g., 0) and the color (e.g., red) that is indicative of the highest first optical property values (e.g., 0.16), with colors between violet and red being indicative of first optical property values between the highest and lowest values (e.g., between 0 and 0.16). Alternatively, as shown, the third hyperspectral data cube 810 can use textures or other indicia that are indicative of the first optical property.

The third hyperspectral data cube 810 (FIG. 8A) is obtained using a Monte-Carlo based inversion model. More specifically, an inversion algorithm compares the first diffuse reflectance values at the first spatial frequency for each of the plurality of sequential wavelengths of light to a look-up-table (e.g., that is stored in the memory device 184 of the controller 180). The look-up-table comprises predetermined optical properties that were generated by Monte Carlo simulations. Based on the comparison to the look-up-table, the controller 180 can determine the first optical property (absorption property a) for each of the plurality of sequential wavelengths of light at each location in the tissue sample 150, and thereby generate the third hyperspectral data cube 810 (FIG. 8A). Alternatively, rather than using the Monte-Carlo based inversion model and look-up-table, the trained neural network described above can be used to generate the third hyperspectral data cube 810 because the neural network is trained using Monte-Carlo simulations.

Step 208 of the method 200 is similar to step 207 and includes determining a second optical property at each location in the tissue sample 150 based on the first diffuse reflectance values associated with the first spatial frequency and the second diffuse reflectance values associated with the second spatial frequency. The second optical property can be, for example, a scattering property ($\mu_s'$). In some implementations, step 208 includes generating a fourth hyperspectral data cube indicative of the second optical property based on the first hyperspectral data cube 710 indicative of the first diffuse reflectance values for the first spatial frequency (FIG. 7A) and the second hyperspectral data cube 720 indicative of the second diffuse reflectance values for the second spatial frequency (FIG. 7B).

Figure 8B:
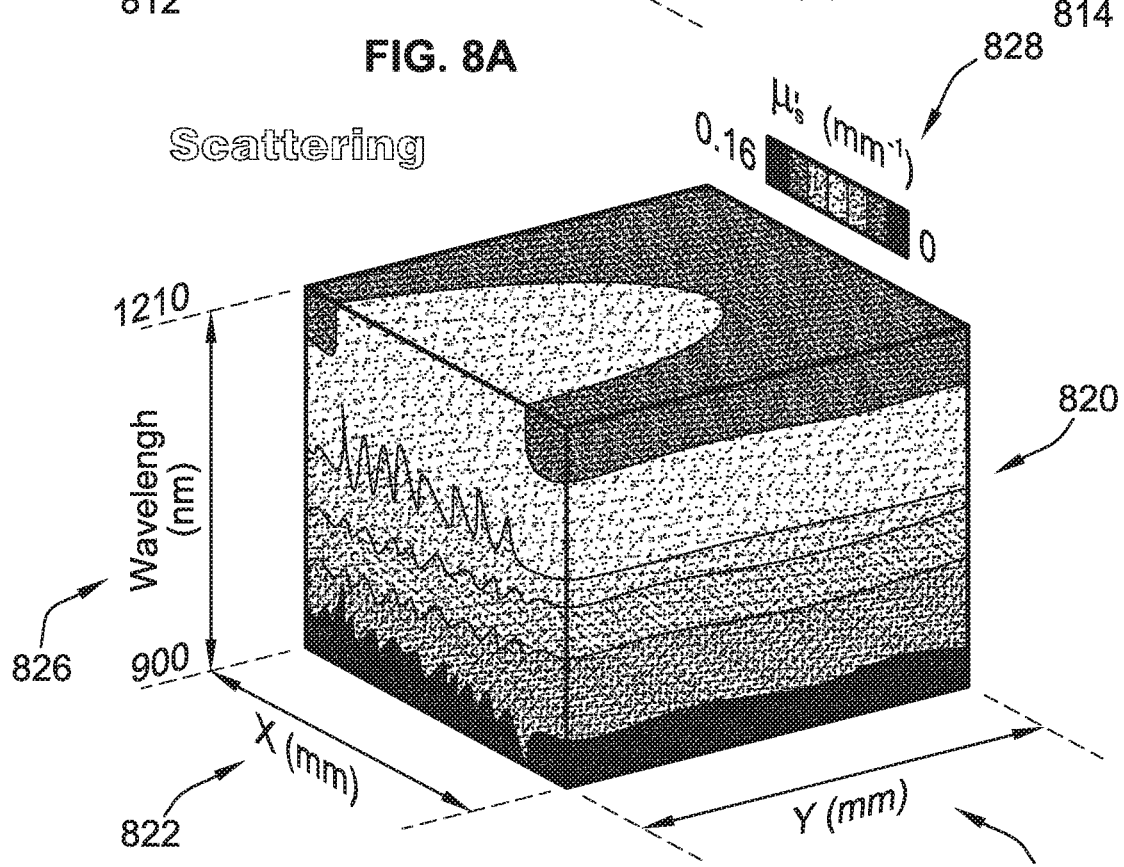
FIG. 8B illustrates a fourth hyperspectral data cube indicative of scattering property values according to some implementations of the present disclosure.

Referring to FIG. 8B, an exemplary fourth hyperspectral data cube 820 indicative of the second optical property, in this example a scattering property $\mu_s'$, is illustrated. The fourth hyperspectral data cube 820 includes a first axis 822 indicative of an x-coordinate on the tissue sample plane 152 (FIG. 1), a second axis 824 indicative of a y-coordinate on the tissue sample plane 152, and a third axis 826 indicative of the plurality of sequential wavelengths of light. The fourth hyperspectral data cube 820 also includes a plurality of colors that are indicative of second optical property at each location within the tissue sample 150, which in this example is a scattering property value. An exemplary legend 828 can indicate that the color (e.g., violet) is indicative of the lowest second optical property value (e.g., 0) and the color (e.g., red) that is indicative of the highest second optical property value (e.g., 2), with colors between violet and red being indicative of second optical property values between the highest and lowest values (e.g., between 0 and 2). Alternatively, as shown, the fourth hyperspectral data cube 812 can use textures or other indicia that are indicative of the second optical property.

Like the third hyperspectral data cube 810 (FIG. 8A), the fourth hyperspectral data cube 820 (FIG. 8B) is obtained using a Monte-Carlo based inversion model. More specifically, an inversion algorithm compares the second diffuse reflectance values at the second spatial frequency for each of the plurality of sequential wavelengths of light to a look-up-table (e.g., that is stored in the memory device 184 of the controller 180). The look-up-table comprises predetermined optical properties that were generated by Monte Carlo simulations. Based on the comparison to the look-up-table, the controller 180 can determine the second optical property (scatting coefficient $\mu_s'$) for each of the plurality of sequential wavelengths of light at each location in the tissue sample 150, and thereby generate the fourth hyperspectral data cube 820 (FIG. 8B).

Step 209 of the method 200 includes determining a molar concentration of one or more chromophores in the tissue sample 150 (FIG. 1) based on the first optical property (step 207) and the second optical property (step 208). The one or more chromophores in the tissue sample 150 can include, for example, one or more lipids, water ($H_2O$), oxy-hemoglobin ($HbO_2$), deoxy-hemoglobin (Hb), or any combination thereof. The molar concentration of the one or more chromophores is determined based on the first optical property (absorption property a) and the second optical property (scattering property $\mu_s'$) using Beer's law (sometimes referred to as the Beer-Lambert law, the Lambert-Beer law, or the Beer-Lambert-Bouguer law). Beer's law defines a relationship between the molar concentration of a material and the absorption of light having a given wavelength passing through the material. Each of the one or more chromophores has a known extinction coefficient (also referred to as molar absorptivity) that has a constant value. As described above, in contrast to blood, water and lipids have distinct optical absorption characteristics at SWIR wavelengths of light. The molar concentration of each of the one or more chromophores can be determined by least squares fitting of the absorption property values a at different ones of the plurality of sequential wavelengths and known extinction coefficients for each chromophore (e.g., that are stored in memory device 184 of the controller 180).

Figure 9A:
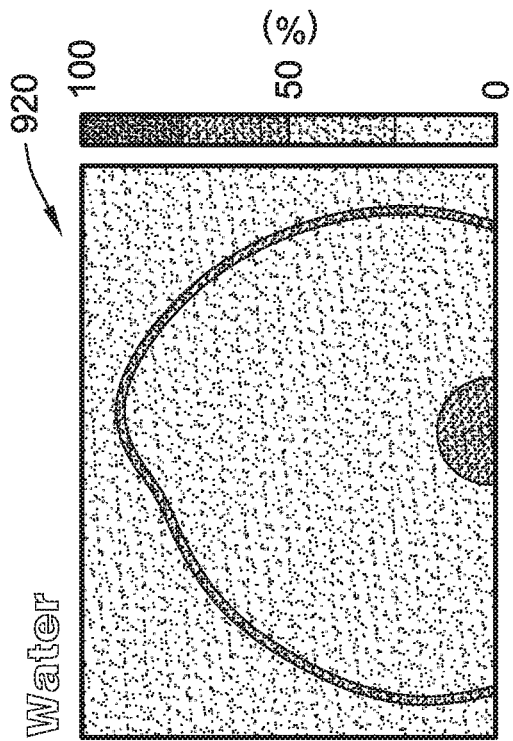
FIG. 9A illustrates a two-dimensional plot indicative of determined molar concentrations of lipids according to some implementations of the present disclosure.
Figure 9B:
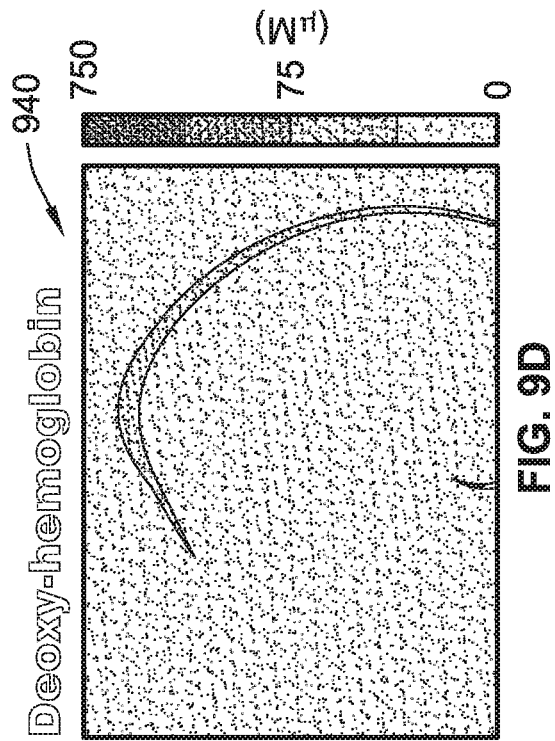
FIG. 9B illustrates a two-dimensional plot indicative of determined molar concentrations of water according to some implementations of the present disclosure.
Figure 9C:
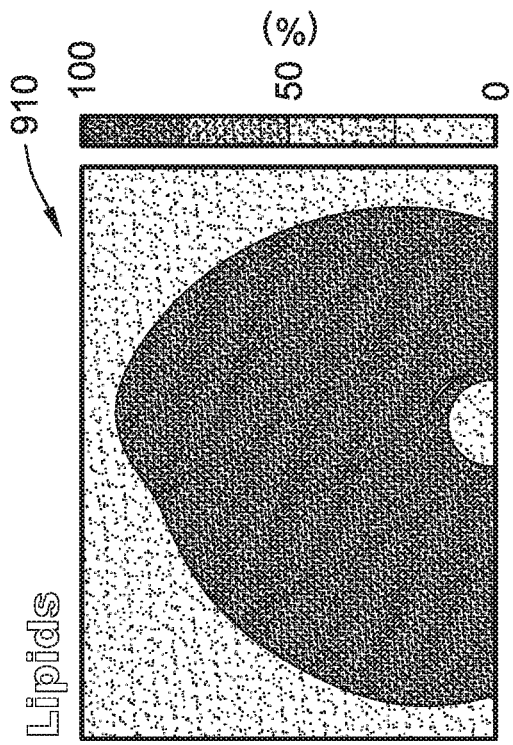
FIG. 9C illustrates a two-dimensional plot indicative of determined molar concentrations of oxy-hemoglobin according to some implementations of the present disclosure.
Figure 9D:
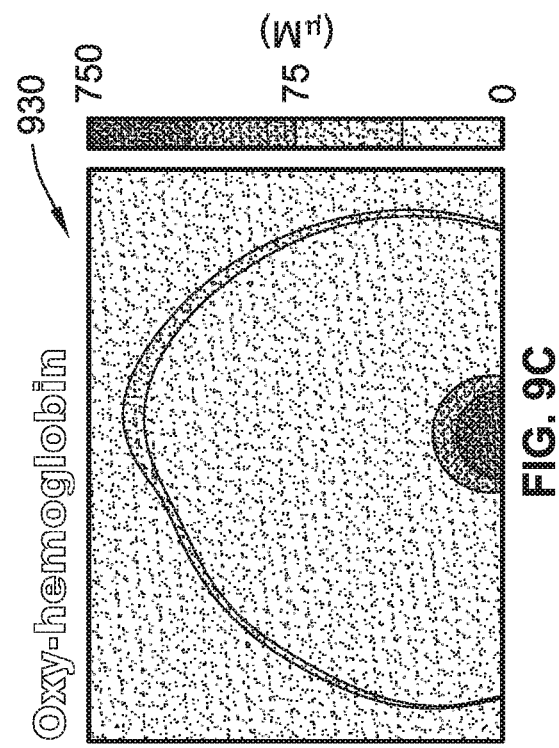
FIG. 9D illustrates a two-dimensional plot indicative of determined molar concentrations of deoxy-hemoglobin according to some implementations of the present disclosure.

Referring to FIGS. 9A-9D, a two-dimensional molar concentration map can be generated for each of the one or more chromophores. FIG. 9A illustrates an exemplary two-dimensional map 910 indicative of a molar concentration of lipids in the tissue sample 150. FIG. 9B illustrates an exemplary two-dimensional map 920 indicative of a molar concentration of water in the tissue sample 150. FIG. 9C illustrates an exemplary two-dimensional map 930 indicative of a molar concentration of oxy-hemoglobin in the tissue sample 150. FIG. 9D illustrates an exemplary two-dimensional map 940 indicative of a molar concentration of deoxy-hemoglobin in the tissue sample 150.

Accuracy

To validate the accuracy of the determined molar concentrations of water and lipids, a series of homogeneous phantoms were measured using an imaging system that is the same as, or similar to, the imaging system 100 described herein and a method that is the same as, or similar to, the method 200 described herein. The series of homogeneous phantoms included a first phantom including 10% lipid and 90% water, a second phantom including 20% lipid and 80% water, a third phantom including 30% lipid and 70% water, and a fourth phantom including 40% lipid and 60% water.

Figure 10A:
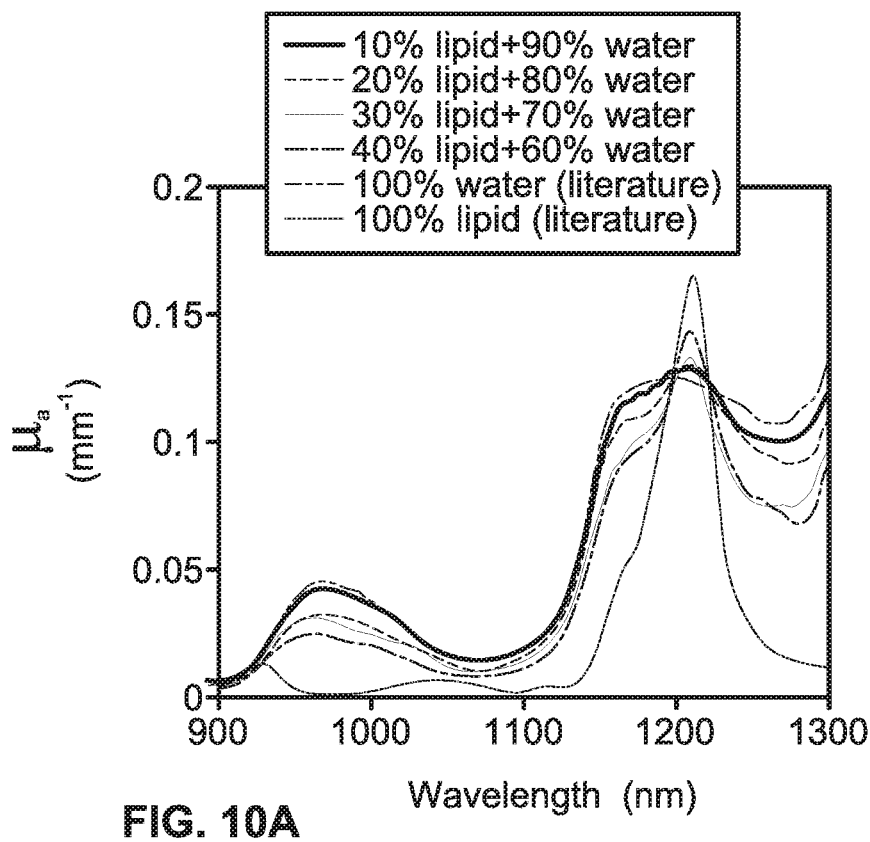
FIG. 10A illustrates determined absorption values plotted against wavelengths for a series of phantoms according to some implementations of the present disclosure.
Figure 10B:
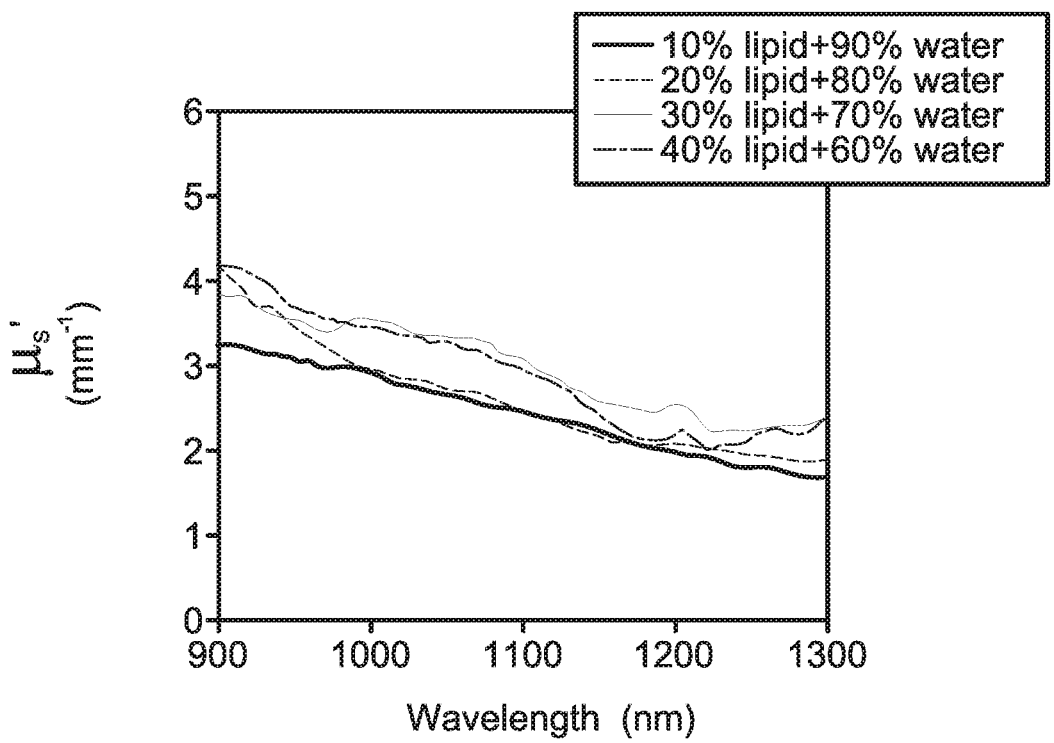
FIG. 10B illustrates determined scattering values plotted against wavelengths for the series of phantoms of FIG. 9A according to some implementations of the present disclosure.

Referring to FIG. 10A, an absorption property value a was determined for a predetermined range of wavelengths between 900 nm and 1,300 nm for each of the series of homogenous phantoms. As shown, the absorption $\mu_s$ peaked at about 970 nm for water and at about 1,210 nm for lipids. The plot includes a NIR window 1110 and a penetration window 1120, shown as boxes. Referring to FIG. 10B, a scattering value $\mu_s'$ was determined for the predetermined range of wavelengths between 900 nm and 1,300 nm for the series of homogenous phantoms. Table 1 includes the known water and lipid content in the series of homogenous phantoms and the water and lipid content as determined using the systems and method described herein ("extracted content").

TABLE 1

| Known Content | | Extracted Content | | Error | |
| --- | --- | --- | --- | --- | --- |
| Water | Lipid | Water | Lipid | Water | Lipid |
| 90.0% | 10.0% | 92.2% | 9.1% | 2.2% | 0.9% |
| 80.0% | 20.0% | 81.3% | 19.0% | 1.3% | 1.0% |
| 70.0% | 30.0% | 66.5% | 28.4% | 3.5% | 1.6% |
| 60.0% | 40.0% | 59.4% | 41.0% | 0.6% | 1.0% |

As shown in Table 1, the average error for water content is 1.9% across the series of homogenous phantom samples and the average error for lipid content is 1.1%. accord the series of homogenous phantom samples.

Tissue Penetration Depth

Figure 11A:
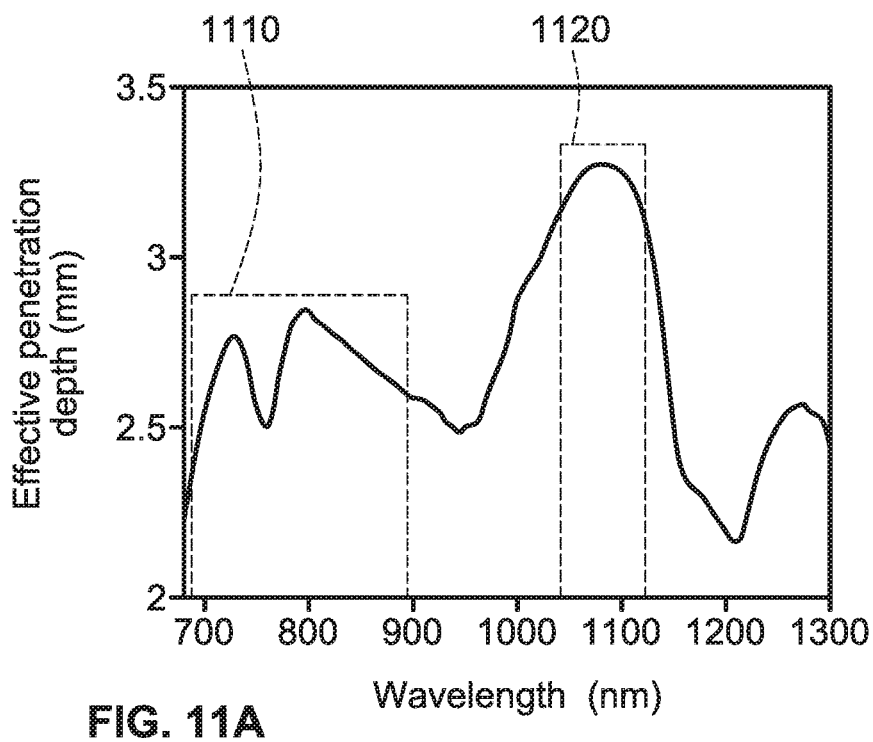
FIG. 11A illustrates an effective penetration depth plotted against wavelength for an NIR window and SWIR window according to some implementations of the present disclosure.
Figure 11B:
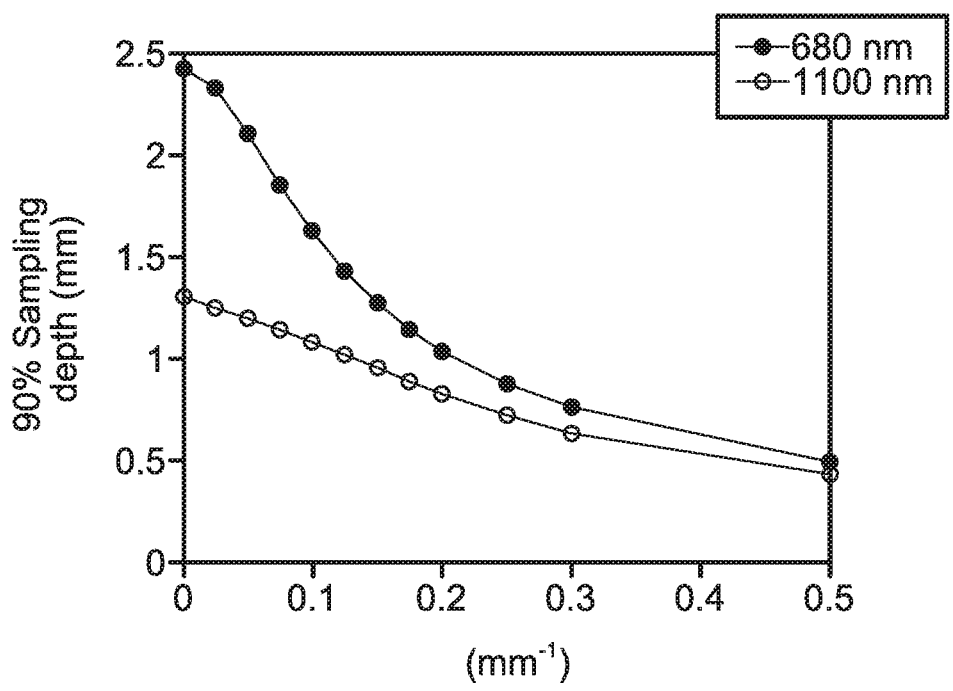
FIG. 11B illustrates sampling depth plotted against spatial frequency for a first wavelength and a second wavelength according to some implementations of the present disclosure.
Figure 11C:
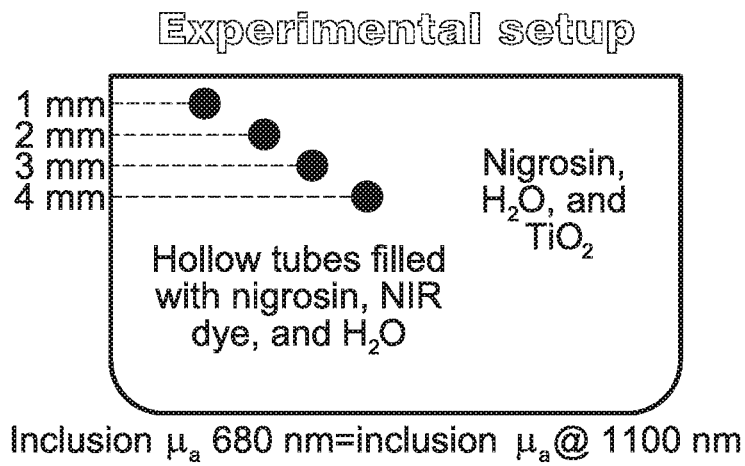
FIG. 11C illustrates an experimental setup for FIG. 11B according to some implementations of the present disclosure.
Figure 11D:
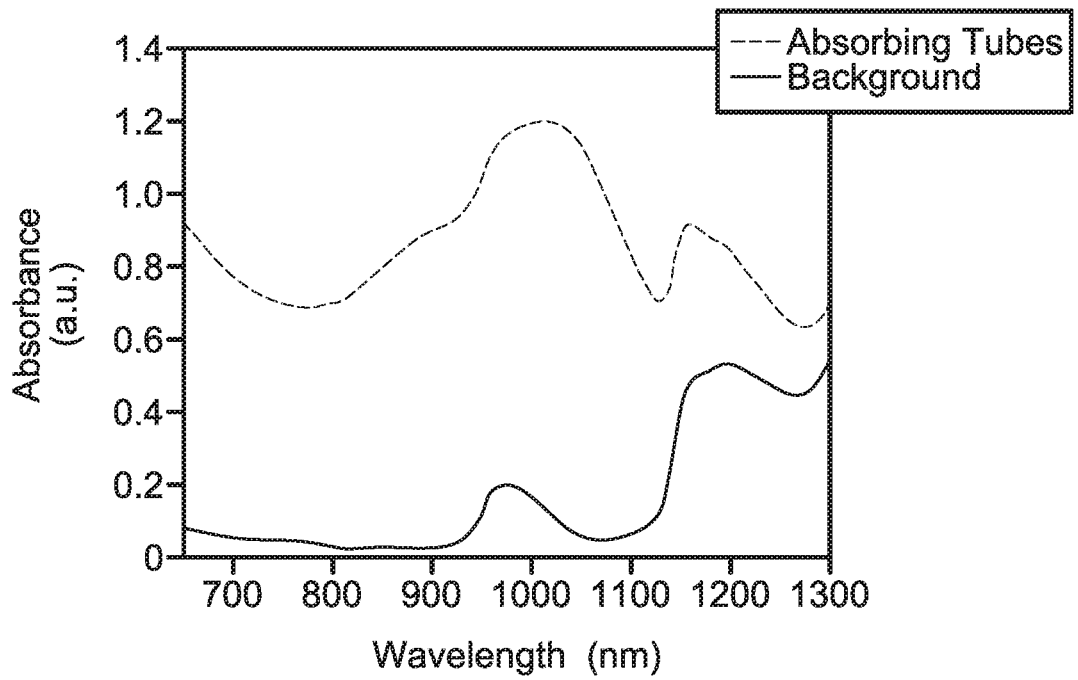
FIG. 11D illustrates absorbance plotted against wavelength for absorbing tubes and a background according to some implementations of the present disclosure.
Figure 11E:
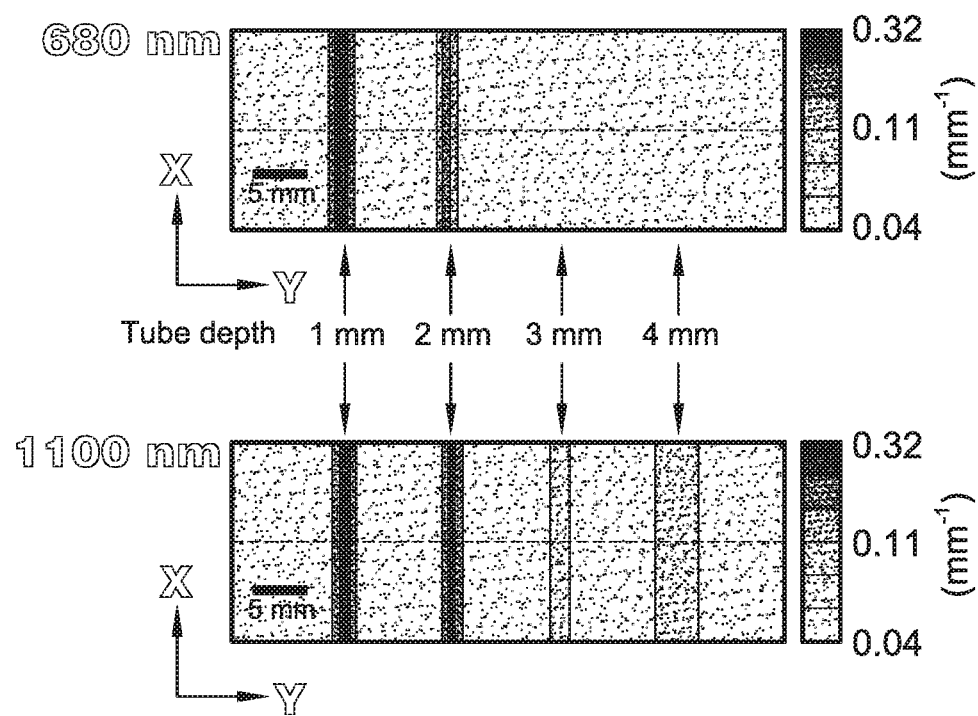
FIG. 11E illustrates an optical absorption map for the first wavelength and an optical absorption map for the second wavelength according to some implementations of the present disclosure.
Figure 11F:
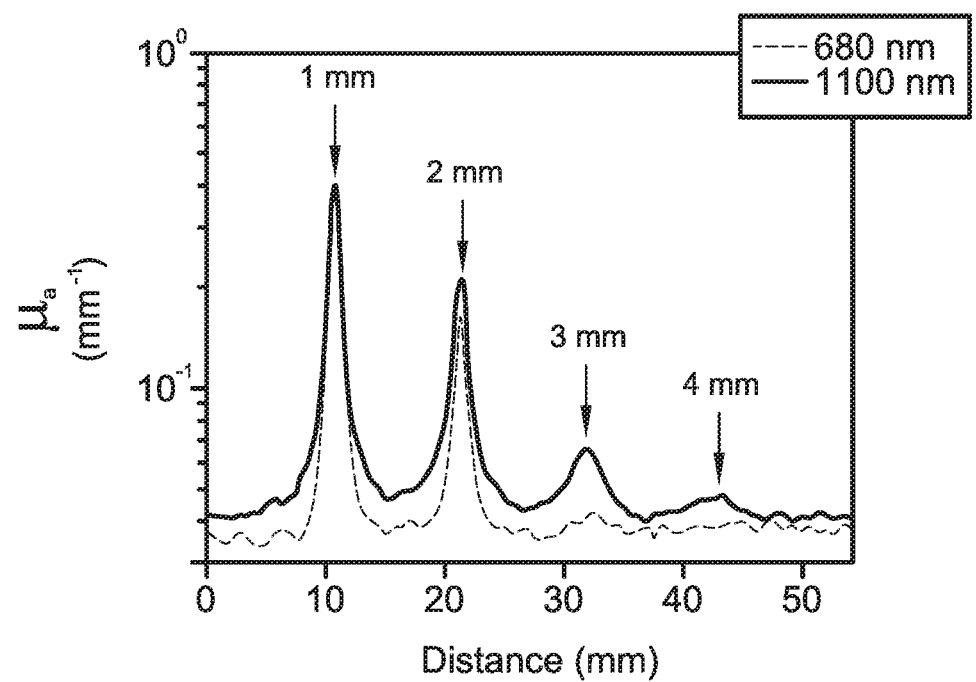
FIG. 11F illustrates line profiles of optical absorption for the first wavelength and the second wavelength according to some implementations of the present disclosure.

As described above, the systems and methods disclosed herein (e.g., imaging system 100 and method 200) can determine molar concentrations of chromophores (e.g., water and/or lipids) within the tissue sample 150 having a sample depth d (FIG. 1). For example, the systems and methods disclosed herein can penetrate up to a sample depth of, for example, at least about 2.5 mm, at least about 3 mm, at least about 3.25 mm, etc. By contrast, conventional hemoglobin imaging systems and methods (e.g., that use wavelengths of light in the near-infrared ("NIR") spectrum or wavelengths of light in the visible spectrum ("VIS")) can only achieve a penetration depth of about 2 mm in a tissue sample. The effective photon penetration depth during planar illumination of a material (e.g., tissue sample), which is function of both an absorption property a and a scattering property $\mu_s'$ is defined by equation 2:

$$\lambda = 1/\sqrt{3\mu_a(\lambda)[\mu_a(\lambda)+\mu_s'(\lambda)]}$$ Equation 2:

As shown in FIG. 11A, a SWIR penetration window near 1,100 nm was identified. As shown in FIG. 11B, the improved penetration depth at a wavelength of 1,110 nm compared to a wavelength at 680 nm was confirmed using the methods described herein (e.g., Monte Carlo simulations). Additionally, a phantom study was conducted to demonstrate the improved penetration depth of the imaging systems (e.g., imaging system 100) and methods described herein that use wavelengths of light within the SWIR band, compared to systems and methods that use the NIR band. Glass capillary tubes containing a mixture of absorbing dye and scattering particles were placed at depths from 1 mm to 4 mm within a homogenous nigrosine-$TiO_2$ phantom. This experimental setup is shown in FIG. 11C. As shown in FIG. 11D, the phantom has nearly identical absorption at both 680 nm and 1.00 nm so as to isolate the effect of optical scattering on penetration depth. The absorption maps and line profiles in FIGS. 11E and 11F show absorption contrast for SWIR at increased depths at a 1,110 nm wavelength compared to at a 680 nm wavelength. The signal-to-background noise ratio ("SBR") was higher in the SWIR penetration window than NIR for all four of the tube depths, as reflected in Table 2 below. The 4 mm tube was not detectable using the NIR band, whereas the 4 mm tube provided a 1.2 SBR when imaging with the SWIR band.

TABLE 2

| SBR | 1 mm | 2 mm | 3 mm | 4 mm |
| --- | --- | --- | --- | --- |
| 680 nm | 9.4 | 3.8 | 1.1 | 1.0 |
| 1,100 nm | 10.0 | 5.1 | 1.6 | 1.2 |
| Improvement | 6.4% | 34.2% | 45.5% | 20.0% |

Exemplary Clinical Applications

The imaging systems and methods disclosed herein (e.g., the imaging system 100 and the method 200) can be used in a variety of non-invasive clinical applications.

For example, the systems and methods disclosed herein can be used to image through skin (e.g., human skin) into superficial veins, and measure and quantify water and lipids within the superficial veins. Conventionally, measurement and quantification of water and lipids in superficial veins required invasive blood draws. Blood draws generally require a sterile environment, proper handling and disposal of bio-hazard materials (e.g., used needles), and can cause a subject (e.g., a human) discomfort or pain. The drawn blood then needs to be analyzed (e.g., sent to a lab) to determine the water and lipid content in the subject's blood. Advantageously, the systems and methods disclosed herein can be used to quickly and non-invasively determine the water and lipid content in in-vivo tissue by imaging through the skin into superficial veins, and accurately quantify the water and lipid content therein.

As another example, the systems and methods disclosed herein can be used to monitor water content in an in vivo tissue sample to study edema and/or acute inflammation. The transient pattern of water accumulation in the tissue, which can be measured using the systems and methods disclosed herein, may be an indicator of inflammation.

As another example, the systems and methods disclosed herein can also be used to monitor and spatially map blood lipid content in in-vivo tissue sample (e.g., from a human). Blood lipid content is a risk factor for cardiovascular disease. Conventionally, blood lipid content is measured via a blood sample drawn from the patient. The imaging systems and methods disclosed herein can be used to measure blood lipid content in a patient without needing to draw blood, and are therefore less invasive.

In another example, the systems and methods disclosed herein can be used to classify lipids in in-vivo tissue samples, including brown adipose tissue ("BAT") and/or white adipose tissue ("WAT") through intact skin. In such implementations, the imaging system can be trained with a machine learning algorithm to identify and differentiate brown or white fat using training data (e.g., training images of brown and white fat).

In yet another example, the systems and methods disclosed herein can be used to measure lipid heterogeneity in tumors. More specifically, the systems and methods described herein can be used to map lipid content through the tumor surface in resected specimens to study the lipid heterogeneity.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

Alternative Implementations

Implementation 1.

A method for measuring water and lipid content in a tissue sample, the method comprising: generating, using a light source and a spatial modulation device, a first plurality of patterns at a first spatial frequency on a tissue sample plane and a second plurality of patterns at a second spatial frequency on the tissue sample plane for a first wavelength of light from a plurality of sequential wavelengths of light, the light source being configured to emit the plurality of sequential wavelengths of light within a predetermined range of wavelengths; obtaining, using an imaging device, (i) first image data reproducible as images of the first plurality of patterns at the first spatial frequency for the first wavelength of light and (ii) second image data reproducible as images of the second plurality of patterns at the second spatial frequency for the first wavelength of light; generating, using a controller, a first demodulated image for the first wavelength of light based on the first image data; determining, using the controller, a first diffuse reflectance value for each of a plurality of locations on the tissue sample plane at the first wavelength of light based on the first demodulated image; generating, using the controller, a second demodulated image for the first wavelength of light based on the second image data; determining, using the controller, a second diffuse reflectance value for each of the plurality of locations on the tissue sample plane for the first wavelength of light based on the second demodulated image; and determining, using the controller, based on the first diffuse reflectance value and the second diffuse reflectance value, (i) a first optical property and (ii) a second optical property for each of the plurality of locations on the tissue sample plane for the first wavelength of light.

Implementation 2.

The method according to implementation 1, wherein the predetermined range of wavelengths of light is between about 900 nm and about 1300 nm.

Implementation 3.

The method according to any one of implementations 1 and 2, wherein the first spatial frequency is 0 $mm^{-1}$, the second spatial frequency is 0.1 $mm^{-1}$, the first optical property is an absorption property, and the second optical property is a scattering property Implementation 4.

The method according to implementation 3, wherein each of the first plurality of patterns and the second plurality of patterns includes a first pattern having a first phase of 0 degrees, a second pattern having a second phase of about 120 degrees, and a third pattern having a third phase of about 240 degrees.

Implementation 5.

The method according to any one of implementations 1-4, wherein the determining the first optical property and the second optical property includes comparing the first diffuse reflectance value and the second diffuse reflectance value for each of the plurality of locations on the tissue sample plane to a look-up table of predetermined values, the look-up table being stored in a memory device of the controller.

Implementation 6.

The method according to any one of implementations 1-5, further comprising generating, using the light source and the spatial modulation device, a third plurality of patterns at the first spatial frequency on a tissue sample plane and a fourth plurality of patterns at the second spatial frequency on the tissue sample plane for a second wavelength of light from the plurality of sequential wavelengths of light; obtaining, using an imaging device, (i) third image data reproducible as images of the third plurality of patterns at the first spatial frequency for the second wavelength of light and (ii) fourth image data reproducible as images of the fourth plurality of patterns at the second spatial frequency for the second wavelength of light; generating, using a controller, a third demodulated image for the second wavelength of light based on the third image data; determining, using the controller, a third diffuse reflectance value for each of a plurality of locations on the tissue sample plane at the second wavelength of light based on the third demodulated image; generating, using the controller, a fourth demodulated image for the second wavelength of light based on the fourth image data; determining, using the controller, a fourth diffuse reflectance value for each of the plurality of locations on the tissue sample plane for the second wavelength of light based on the fourth demodulated image; and determining, using the controller, based on the third diffuse reflectance value and the fourth diffuse reflectance value, (i) a third optical property and (ii) a fourth optical property for each of the plurality of locations on the tissue sample plane for the second wavelength of light.

Implementation 7.

The method according to implementation 6, wherein the first optical property and the second optical property at each of the plurality of locations on the tissue sample plane for the first wavelength of light is associated with a first depth in the tissue sample, and the third optical property and the fourth optical property at each of the plurality of locations on the tissue sample plane for the second wavelength of light is associated with a second depth in the tissue sample that is different than the first depth.

Implementation 8.

The method according to any of implementations 6 and 7, further comprising generating, using the controller, a first hyperspectral data cube including a first axis indicative of an x-coordinate on the tissue sample plane, a second axis indicative of a y-coordinate on the tissue sample plane, a third axis indicative of the first wavelength of light and the second wavelength of light, and a plurality of colors indicative of the first diffuse reflectance values for the first wavelength of light and the third diffuse reflectance values for the second wavelength of light; and generating, using the controller, a second hyperspectral data cube including a first axis indicative of an x-coordinate on the tissue sample plane, a second axis indicative of a y-coordinate on the tissue sample plane, a third axis indicative of the first wavelength of light and the second wavelength of light, and a plurality of colors indicative of the second diffuse reflectance values for the first wavelength of light and the fourth diffuse reflectance values for the second wavelength of light.

Implementation 9.

The method according to implementation 8, further comprising generating, using the controller, a third hyperspectral data cube including a first axis indicative of an x-coordinate on the tissue sample, a second axis indicative of a y-coordinate on the tissue sample, a third axis indicative of the first wavelength of light and the second wavelength of light, and a plurality of colors indicative of the first optical property and the third optical property; and generating, using the controller, a fourth hyperspectral data cube including a first axis indicative of an x-coordinate on the tissue sample, a second axis indicative of a y-coordinate on the tissue sample, a third axis indicative of the first wavelength of light and the second wavelength of light, and a plurality of colors indicative of the second optical property and the fourth optical property.

Implementation 10.

The method according to any one of implementations 1-9, further comprising determining a molar concentration of a chromophore based on the first optical property and the second optical property; and generating one or more graphs indicative of the determined molar concentration of the chromophore.

Implementation 11.

The method according to implementation 10, wherein the chromophore is a lipid, water, oxy-hemoglobin, deoxy-hemoglobin, or any combination thereof.

Implementation 12.

The method according to any one of implementations 1-11, further comprising obtaining, using the imaging device, phantom image data reproducible as one or more images of a phantom having a predetermined optical property; determining, using the controller, an instrument response based on the phantom image data; and calibrating, using the controller, the first demodulated image and the second demodulated image based on the instrument response.

Implementation 13.

An imaging system for measuring water and blood lipid content in a tissue sample comprises: a light source configured to emit a plurality of sequential wavelengths of light at a predetermined interval, each of the plurality of sequential wavelengths of light being within a predetermined range of wavelengths; a spatial modulation device configured to direct each of the plurality of sequential wavelengths of light emitted from the light source onto a tissue sample plane and cause each of the plurality of sequential wavelengths of light to generate: (i) a first plurality of patterns on the issue sample plane at a first spatial frequency, and (ii) a second plurality of patterns on the tissue sample plane at a second spatial frequency; an imaging device configured to generate (i) first image data reproducible as images of each of the first plurality of patterns and (ii) second image data reproducible as images each of the second plurality of patterns; and a controller including one or more processors and one or more memory devices, at least one of the one or more memory devices storing computer-readable instructions configured to cause at least one of the one or more processors to: generate, using the first image data, a first demodulated image associated with the first spatial frequency for each of the plurality of sequential wavelengths of light; determine a first diffuse reflectance value for each of a plurality of locations on the tissue sample plane for each of the plurality of sequential wavelength based on the first demodulated image; generate, using the second image data, a second demodulated image associated with the second spatial frequency for each of the plurality of sequential wavelengths of light; determine a second diffuse reflectance value for each of the plurality of locations on the tissue sample plane for each of the plurality of sequential wavelength based on the second demodulated image; and determine, based on the first diffuse reflectance value and the second diffuse reflectance value, (i) a first optical property and (ii) a second optical property for each of the plurality of locations on the sample plane for each of the plurality of sequential wavelengths of light.

Implementation 14.

The imaging system according to implementation 13, wherein the predetermined range of wavelengths is between about 900 nm and about 1,300 nm.

Implementation 15.

The imaging system according to any one of implementations 13 and 14, wherein for each of the plurality of sequential wavelengths of light (i) the first plurality of patterns includes a first pattern having a first phase, a second pattern having a second phase, and a third pattern having a third phase and (ii) the second plurality of patterns includes a first pattern having the first phase, a second pattern having the second phase, and a third pattern having the third phase.

Implementation 16.

The imaging system according to implementation 15, wherein the first phase is 0 degrees, the second phase is 120 degrees, and the third phase is 240 degrees.

Implementation 17.

The imaging system according to any one of implementations 13-16, wherein the predetermined interval is 5 nm.

Implementation 18.

The imaging system according to any one of implementations 13-17, wherein the first spatial frequency is 0 mm$^{-1}$, the second spatial frequency is 0.1 mm$^{1}$.

Implementation 19.

The imaging system according to any one of implementations 13-18, wherein the first optical property is an absorption property and the second optical property is a scattering property.

Implementation 20.

The imaging system according to any one of implementations 13-19, wherein the imaging device is a camera having a spectral sensitivity between about 300 nm and about 1,600 nm.

Implementation 21.

The imaging system according to any one of implementations 13-20, wherein the spatial modulation device includes one or more digital micromirrors.

Implementation 22.

The imaging system according to any one of implementations 13-21, wherein the light source is a laser configured to emit laser pulses within the predetermined range of wavelengths at the predetermined interval.

Implementation 23.

The imaging system according to implementation 22, further comprising a diffuser, a collimating lens, and a first polarizer positioned between the light source and the spatial modulation device.

Implementation 24.

The imaging system according to any one of implementations 13-22, further comprising one or more mirrors configured to aid the spatial modulation device in directing the plurality of sequential wavelengths of light onto the tissue sample plane.

Implementation 25.

The imaging system according to implementation 24, further comprising a lens positioned between the spatial modulation device at one of the one or more mirrors and a polarizer positioned between the tissue sample plane and the imaging device.

Implementation 26.

The imaging system according to any one of implementations 13-25, wherein the one or more processors are configured to generate a first hyperspectral data cube including a first axis indicative of an x-coordinate on the tissue sample, a second axis indicative of a y-coordinate on the tissue sample, a third axis indicative of the plurality of wavelengths of light, and a plurality of colors indicative of the first optical property for each of the plurality of sequential wavelengths of light; and generate a second hyperspectral data cube including a first axis indicative of an x-coordinate on the tissue sample, a second axis indicative of a y-coordinate on the tissue sample, a third axis indicative of the plurality of wavelengths of light, and a plurality of colors indicative of the second optical property for each of the plurality of sequential wavelengths of light.

Implementation 27.

The imaging system according to any one of implementations 13-26, wherein the one or more processors are configured to determine a molar concentration of one or more chromophores in the tissue sample based on the first optical property and the second optical property; and generate one or more graphs indicative of the determined molar concentration of the one or more chromophores.

Implementation 28.

The imaging system according to implementation 27, wherein the one or more chromophores includes water, lipids, deoxy-hemoglobin, oxy-hemoglobin, or any combination thereof.

It is contemplated that any element or any portion thereof from any of implementations 1-28 above can be combined with any other element or elements or portion(s) thereof from any of implementations 1-28 to form an implementation of the present disclosure.

What is claimed is:

1. A method for measuring blood lipid content in a blood vessel in a tissue sample, the method comprising:
   generating, using a light source and a spatial modulation device, a first plurality of patterns at a first spatial frequency on a plane of a tissue sample of a subject and a second plurality of patterns at a second spatial frequency on the plane of the tissue sample for a first wavelength of light from a plurality of sequential wavelengths of light, the light source being configured to emit the plurality of sequential wavelengths of light within a predetermined range of wavelengths;
   obtaining, using an imaging device, (i) first image data reproducible as images of the first plurality of patterns at the first spatial frequency for the first wavelength of light and (ii) second image data reproducible as images of the second plurality of patterns at the second spatial frequency for the first wavelength of light;
   generating, using a controller, a first demodulated image for the first wavelength of light based on the first image data;
   determining, using the controller, a first diffuse reflectance value for each of a plurality of locations on the plane of the tissue sample at the first wavelength of light based on the first demodulated image;
   generating, using the controller, a second demodulated image for the first wavelength of light based on the second image data;
   determining, using the controller, a second diffuse reflectance value for each of the plurality of locations on the plane on the tissue sample for the first wavelength of light based on the second demodulated image;
   determining, using the controller, based on the first diffuse reflectance value and the second diffuse reflectance value, (i) a first optical property and (ii) a second optical property for each of the plurality of locations on the plane of the tissue sample for the first wavelength of light;
   determining a molar concentration for a plurality of chromophores based on the first optical property and the second optical property, the plurality of chromophores including a lipid, oxy-hemoglobin, and de-oxy hemoglobin;
   identifying a blood vessel in the tissue sample based at least in part on the determined first optical property, the determined second optical property, or both at each of the plurality of locations on the plane of the tissue sample; and
   determining a blood lipid content in the identified blood vessel in the tissue sample based on the molar concentration of the plurality of chromophores.

2. The method of claim 1, wherein the predetermined range of wavelengths of light is between about 900 nm and about 1,300 nm.

3. The method of claim 1, wherein the first spatial frequency is 0 mm$^{-1}$ the second spatial frequency is 0.1 mm$^{-1}$, the first optical property is an absorption property, and the second optical property is a scattering property.

4. The method of claim 3, wherein each of the first plurality of patterns and the second plurality of patterns includes a first pattern having a first phase of 0 degrees, a second pattern having a second phase of about 120 degrees, and a third pattern having a third phase of about 240 degrees.

5. The method of claim 1, wherein the determining the first optical property and the second optical property includes comparing the first diffuse reflectance value and the second diffuse reflectance value for each of the plurality of locations on the plane of the tissue sample to a look-up table of predetermined values, the look-up table being stored in a memory device of the controller.

6. The method of claim 1, further comprising:
   generating, using the light source and the spatial modulation device, a third plurality of patterns at the first spatial frequency on the plane of the tissue sample and a fourth plurality of patterns at the second spatial frequency on the plane of the tissue sample for a second wavelength of light from the plurality of sequential wavelengths of light;
   obtaining, using an imaging device, (i) third image data reproducible as images of the third plurality of patterns at the first spatial frequency for the second wavelength of light and (ii) fourth image data reproducible as images of the fourth plurality of patterns at the second spatial frequency for the second wavelength of light;
   generating, using a controller, a third demodulated image for the second wavelength of light based on the third image data;
   determining, using the controller, a third diffuse reflectance value for each of a plurality of locations on the plane of the tissue sample at the second wavelength of light based on the third demodulated image;
   generating, using the controller, a fourth demodulated image for the second wavelength of light based on the fourth image data;
   determining, using the controller, a fourth diffuse reflectance value for each of the plurality of locations on the plane of the tissue sample for the second wavelength of light based on the fourth demodulated image; and
   determining, using the controller, based on the third diffuse reflectance value and the fourth diffuse reflectance value, (i) a third optical property and (ii) a fourth optical property for each of the plurality of locations on the plane of the tissue sample for the second wavelength of light.

7. The method of claim 6, wherein the first optical property and the second optical property at each of the plurality of locations on the plane of the tissue sample for the first wavelength of light is associated with a first depth in the tissue sample, and the third optical property and the fourth optical property at each of the plurality of locations on the plane of the tissue sample for the second wavelength of light is associated with a second depth in the tissue sample that is different than the first depth.

8. The method of claim 6, further comprising:
   generating, using the controller, a first hyperspectral data cube including a first axis indicative of an x-coordinate on the plane of the tissue sample, a second axis indicative of a y-coordinate on the plane of the tissue sample, a third axis indicative of the first wavelength of light and the second wavelength of light, and a plurality of colors indicative of the first diffuse reflectance values for the first wavelength of light and the third diffuse reflectance values for the second wavelength of light; and
   generating, using the controller, a second hyperspectral data cube including a first axis indicative of an x-coordinate on the plane of the tissue sample, a second axis indicative of a y-coordinate on the plane of the tissue sample, a third axis indicative of the first wavelength of light and the second wavelength of light, and a plurality of colors indicative of the second diffuse reflectance values for the first wavelength of light and the fourth diffuse reflectance values for the second wavelength of light.

9. The method of claim 8, further comprising:
generating, using the controller, a third hyperspectral data cube including a first axis indicative of an x-coordinate on the tissue sample, a second axis indicative of a y-coordinate on the tissue sample, a third axis indicative of the first wavelength of light and the second wavelength of light, and a plurality of colors indicative of the first optical property and the third optical property; and
generating, using the controller, a fourth hyperspectral data cube including a first axis indicative of an x-coordinate on the tissue sample, a second axis indicative of a y-coordinate on the tissue sample, a third axis indicative of the first wavelength of light and the second wavelength of light, and a plurality of colors indicative of the second optical property and the fourth optical property.

10. The method of claim 1, further comprising: generating one or more graphs indicative of the determined blood lipid content in the identified blood vessel in the tissue sample of the subject.

11. The method of claim 10, wherein the blood lipid content is a molar concentration.

12. The method of claim 1, further comprising
obtaining, using the imaging device, phantom image data reproducible as one or more images of a phantom having a predetermined optical property;
determining, using the controller, an instrument response based on the phantom image data; and
calibrating, using the controller, the first demodulated image and the second demodulated image based on the instrument response.

13. An imaging system for measuring blood lipid content in a blood vessel in a tissue sample, the imaging system comprising:
a light source configured to emit a plurality of sequential wavelengths of light at a predetermined interval, each of the plurality of sequential wavelengths of light being within a predetermined range of wavelengths;
a spatial modulation device configured to direct each of the plurality of sequential wavelengths of light emitted from the light source onto a tissue sample plane and cause each of the plurality of sequential wavelengths of light to generate: (i) a first plurality of patterns on the issue sample plane at a first spatial frequency, and (ii) a second plurality of patterns on the tissue sample plane at a second spatial frequency;
an imaging device configured to generate (i) first image data reproducible as images of each of the first plurality of patterns and (ii) second image data reproducible as images each of the second plurality of patterns; and
a controller including one or more processors and one or more memory devices, at least one of the one or more memory devices storing computer-readable instructions configured to cause at least one of the one or more processors to:
generate, using the first image data, a first demodulated image associated with the first spatial frequency for each of the plurality of sequential wavelengths of light;
determine a first diffuse reflectance value for each of a plurality of locations on the tissue sample plane for each of the plurality of sequential wavelength based on the first demodulated image;
generate, using the second image data, a second demodulated image associated with the second spatial frequency for each of the plurality of sequential wavelengths of light;
determine a second diffuse reflectance value for each of the plurality of locations on the tissue sample plane for each of the plurality of sequential wavelength based on the second demodulated image;
determine, based on the first diffuse reflectance value and the second diffuse reflectance value, (i) a first optical property and (ii) a second optical property for each of the plurality of locations on the sample plane for each of the plurality of sequential wavelengths of light;
determine a molar concentration for a plurality of chromophores based on the first optical property and the second optical property, the plurality of chromophores including a lipid, oxy-hemoglobin, and de-oxy hemoglobin;
identify a blood vessel in the tissue sample based at least in part on the determined first optical property, the determined second optical property, or both at each of the plurality of locations on the plane of the tissue sample; and
determine a blood lipid content in the identified blood vessel in the tissue sample based on the molar concentration of the plurality of chromophores.

14. The imaging system of claim 13, wherein the predetermined range of wavelengths is between about 900 nm and about 1,300 nm.

15. The imaging system of claim 13, wherein for each of the plurality of sequential wavelengths of light (i) the first plurality of patterns includes a first pattern having a first phase, a second pattern having a second phase, and a third pattern having a third phase and (ii) the second plurality of patterns includes a first pattern having the first phase, a second pattern having the second phase, and a third pattern having the third phase.

16. The imaging system of claim 15, wherein the first phase is 0 degrees, the second phase is 120 degrees, and the third phase is 240 degrees.

17. The imaging system of claim 13, wherein the predetermined interval is 5 nm.

18. The imaging system of claim 13, wherein the first spatial frequency is 0 $mm^{-1}$, the second spatial frequency is 0.1 $mm^{-1}$.

19. The imaging system of claim 13, wherein the first optical property is an absorption property and the second optical property is a scattering property.

20. The imaging system of claim 13, wherein the imaging device is a camera having a spectral sensitivity between about 300 nm and about 1,600 nm.

21. The imaging system of claim 13, wherein the spatial modulation device includes one or more digital micromirrors.

22. The imaging system of claim 13, wherein the light source is a laser configured to emit laser pulses within the predetermined range of wavelengths at the predetermined interval.

23. The imaging system of claim 22, further comprising a diffuser, a collimating lens, and a first polarizer positioned between the light source and the spatial modulation device.

24. The imaging system of claim 13, further comprising one or more mirrors configured to aid the spatial modulation device in directing the plurality of sequential wavelengths of light onto the tissue sample plane.

25. The imaging system of claim 24, further comprising a lens positioned between the spatial modulation device at one of the one or more mirrors and a polarizer positioned between the tissue sample plane and the imaging device.

26. The imaging system of claim 13, wherein the one or more processors are configured to:
generate a first hyperspectral data cube including a first axis indicative of an x-coordinate on the tissue sample, a second axis indicative of a y-coordinate on the tissue sample, a third axis indicative of the plurality of wavelengths of light, and a plurality of colors indicative of the first optical property for each of the plurality of sequential wavelengths of light; and
generate a second hyperspectral data cube including a first axis indicative of an x-coordinate on the tissue sample, a second axis indicative of a y-coordinate on the tissue sample, a third axis indicative of the plurality of wavelengths of light, and a plurality of colors indicative of the second optical property for each of the plurality of sequential wavelengths of light.

* * * * *